(12) United States Patent
Narvekar et al.

(10) Patent No.: US 11,498,709 B2
(45) Date of Patent: Nov. 15, 2022

(54) METHOD FOR CLOSING CARTRIDGES, SUPPORTING STRUCTURE FOR SUPPORTING CARTRIDGE CLOSURES AND TRANSPORT OR PACKAGING CONTAINER

(71) Applicant: SCHOTT POONAWALLA PRIVATE LIMITED, Mumbai (IN)

(72) Inventors: Anil Narayan Narvekar, Goa (IN); Pratul Prakash Potdar, Nani Daman (IN)

(73) Assignee: Schott Poonawalla Private Limted, Mumbia (IN)

( * ) Notice: Subject to any disclaimer, the term of this patent is extended or adjusted under 35 U.S.C. 154(b) by 0 days.

(21) Appl. No.: 16/839,100

(22) Filed: Apr. 3, 2020

(65) Prior Publication Data
US 2020/0277089 A1 Sep. 3, 2020

Related U.S. Application Data

(62) Division of application No. 15/564,305, filed as application No. PCT/IN2016/000099 on Apr. 18, 2016, now Pat. No. 10,800,557.

(30) Foreign Application Priority Data

Apr. 17, 2015 (IN) .......................... 1590/MUM/2015
Oct. 16, 2015 (WO) ................. PCT/IN2015/000394

(51) Int. Cl.
*B65B 43/54* (2006.01)
*B65B 7/16* (2006.01)
(Continued)

(52) U.S. Cl.
CPC .............. *B65B 7/161* (2013.01); *A61J 1/062* (2013.01); *A61J 1/1412* (2013.01); *A61M 5/008* (2013.01);
(Continued)

(58) Field of Classification Search
CPC . B65B 7/16; B65B 7/161; B01L 3/508; B01L 3/5082; A61J 1/06; A61J 1/062; A61J 1/065; A61J 1/067
(Continued)

(56) References Cited

U.S. PATENT DOCUMENTS 3,643,812 A 2/1972 Mander et al.
8,118,167 B2 2/2012 Togashi et al.
(Continued)

FOREIGN PATENT DOCUMENTS

WO 2009015862 A1 2/2009
WO 2013103079 7/2013

OTHER PUBLICATIONS

Search Report for corresponding Brazilian Application No. BR112017022251-5 dated May 19, 2020 and its English translation.
(Continued)

*Primary Examiner* — Chelsea E Stinson
(74) *Attorney, Agent, or Firm* — Taylor IP, P.C.

(57) ABSTRACT

A transport or packaging container accommodating a plurality of supporting structures for closures, for transporting or packaging closures for closing cartridges for use in pharmaceutical, medical or cosmetic applications, in which the transport or packaging container is box-shaped and includes a bottom, which is closed or sealed by a seal, upstanding lower side-walls extending essentially perpendicularly from the bottom, a circumferential supporting step extending horizontally from the upstanding lower side-walls, upper side-walls extending upward from said circumferential supporting step, and a circumferential flange formed at upper ends of the upper side-walls; and the plurality of supporting structures for closures is accommodated inside the transport or packaging container.

18 Claims, 27 Drawing Sheets

(51) Int. Cl.
*A61M 5/00* (2006.01)
*B65B 31/02* (2006.01)
*B65B 3/00* (2006.01)
*B01L 3/00* (2006.01)
*B01L 9/06* (2006.01)
*B65B 39/00* (2006.01)
*A61J 1/06* (2006.01)
*A61J 1/14* (2006.01)
*B65B 7/28* (2006.01)
*B65B 43/59* (2006.01)
*B65B 55/04* (2006.01)
*B65B 55/20* (2006.01)
*B65B 61/20* (2006.01)

(52) U.S. Cl.
CPC .............. *B01L 3/5082* (2013.01); *B01L 3/523* (2013.01); *B01L 9/06* (2013.01); *B65B 3/003* (2013.01); *B65B 7/2821* (2013.01); *B65B 31/027* (2013.01); *B65B 39/00* (2013.01); *B65B 43/54* (2013.01); *B65B 43/59* (2013.01); *B65B 55/04* (2013.01); *B65B 55/20* (2013.01); *B65B 61/207* (2013.01); *B01L 2200/185* (2013.01); *B01L 2300/042* (2013.01); *B01L 2300/044* (2013.01); *B01L 2300/0835* (2013.01); *B01L 2300/123* (2013.01); *B65B 2039/009* (2013.01)

(58) Field of Classification Search
USPC .......................................................... 53/471
See application file for complete search history.

(56) References Cited

U.S. PATENT DOCUMENTS

| | | | |
|---|---|---|---|
| 8,360,238 | B2 | 1/2013 | Nicoletti |
| 8,561,828 | B2 | 10/2013 | Krauss et al. |
| 8,978,344 | B2 | 3/2015 | Krauss et al. |
| 9,415,155 | B2 | 8/2016 | Togashi et al. |
| 2001/0008962 | A1 | 7/2001 | Forsberg et al. |
| 2005/0214924 | A1 | 9/2005 | Glaser et al. |
| 2009/0095647 | A1 | 4/2009 | Togashi et al. |
| 2011/0192756 | A1* | 8/2011 | Hill ...................... A61M 5/008 206/515 |
| 2012/0248057 | A1 | 10/2012 | Bogle et al. |
| 2013/0048531 | A1 | 2/2013 | Nicoletti |
| 2013/0161225 | A1 | 6/2013 | Lepot |
| 2014/0027332 | A1* | 1/2014 | Pawlowski ........... A61M 5/008 206/438 |
| 2014/0069062 | A1 | 3/2014 | Bogle et al. |
| 2015/0089830 | A1 | 4/2015 | Wissner et al. |
| 2015/0272827 | A1 | 10/2015 | Tsukiji |
| 2016/0200461 | A1* | 7/2016 | Broadbent ............ B65B 55/027 53/426 |

OTHER PUBLICATIONS

Official Action for corresponding Chile Application No. 201702586 dated Nov. 11, 2018.

PCT/IN2016/000099; PCT International Search Report and Written Opinion of the International Searching Authority dated Aug. 29, 2016.

PCT/IN2016/000099; PCT International Preliminary Report on Patentability dated Jul. 18, 2017.

* cited by examiner

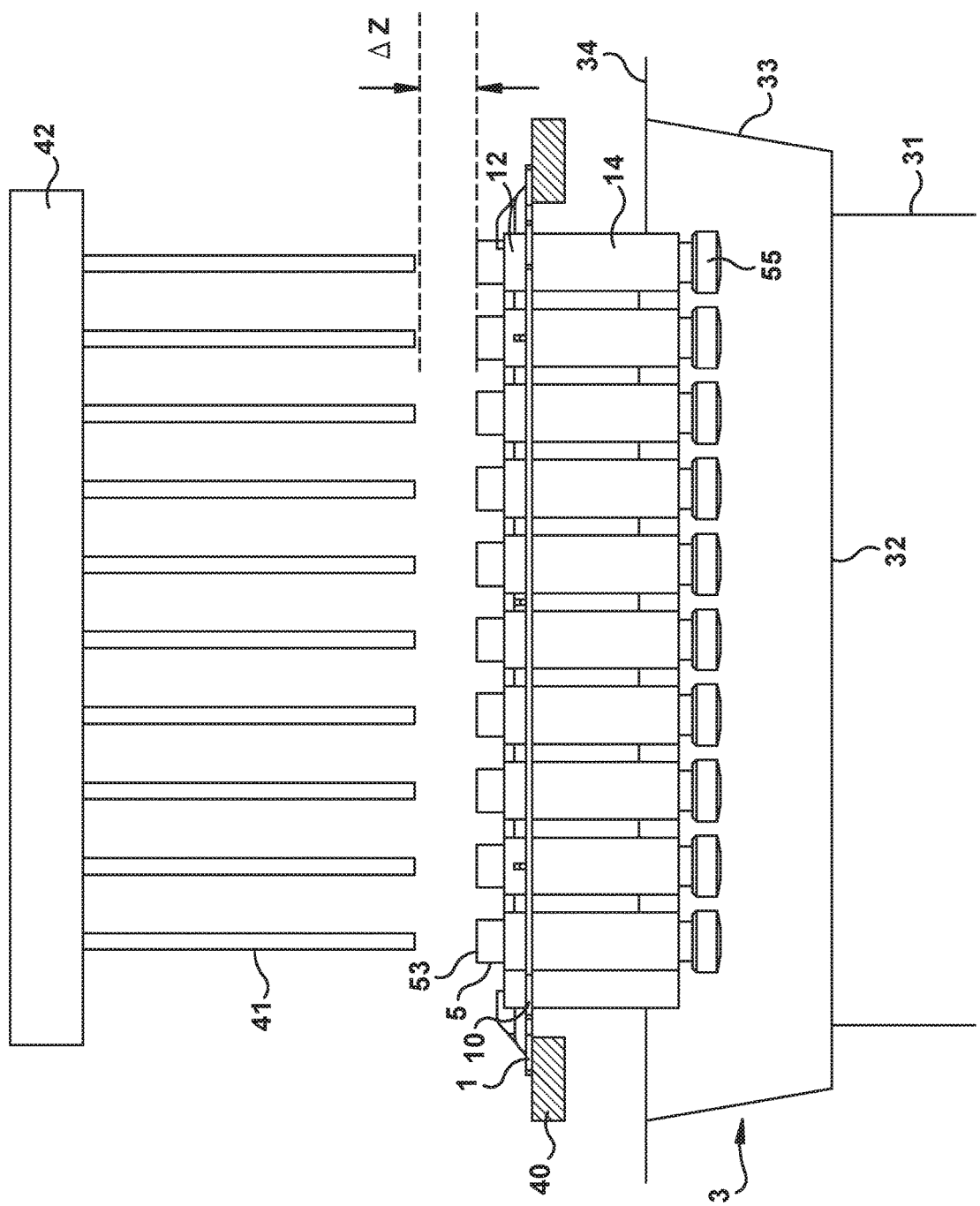

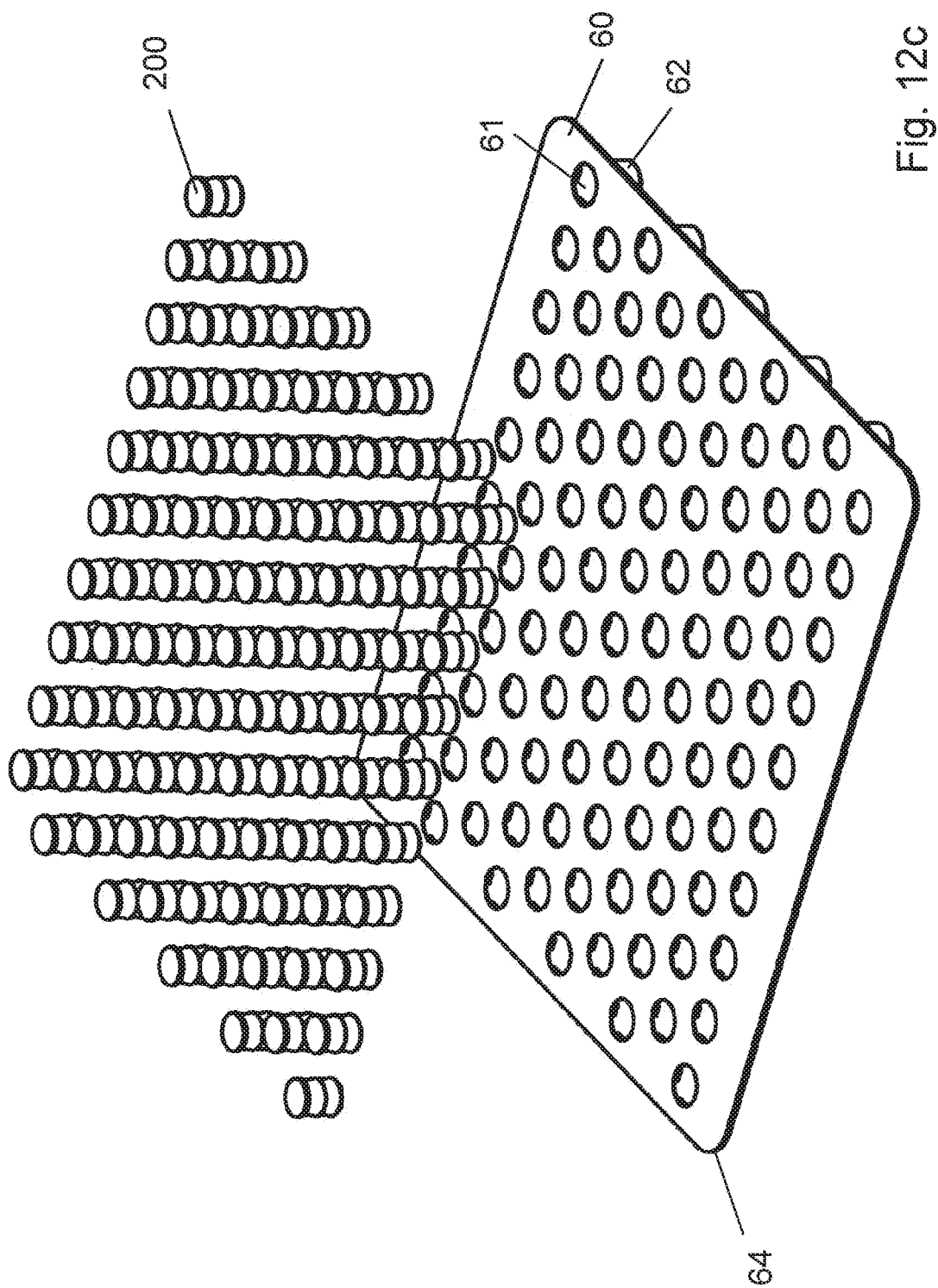

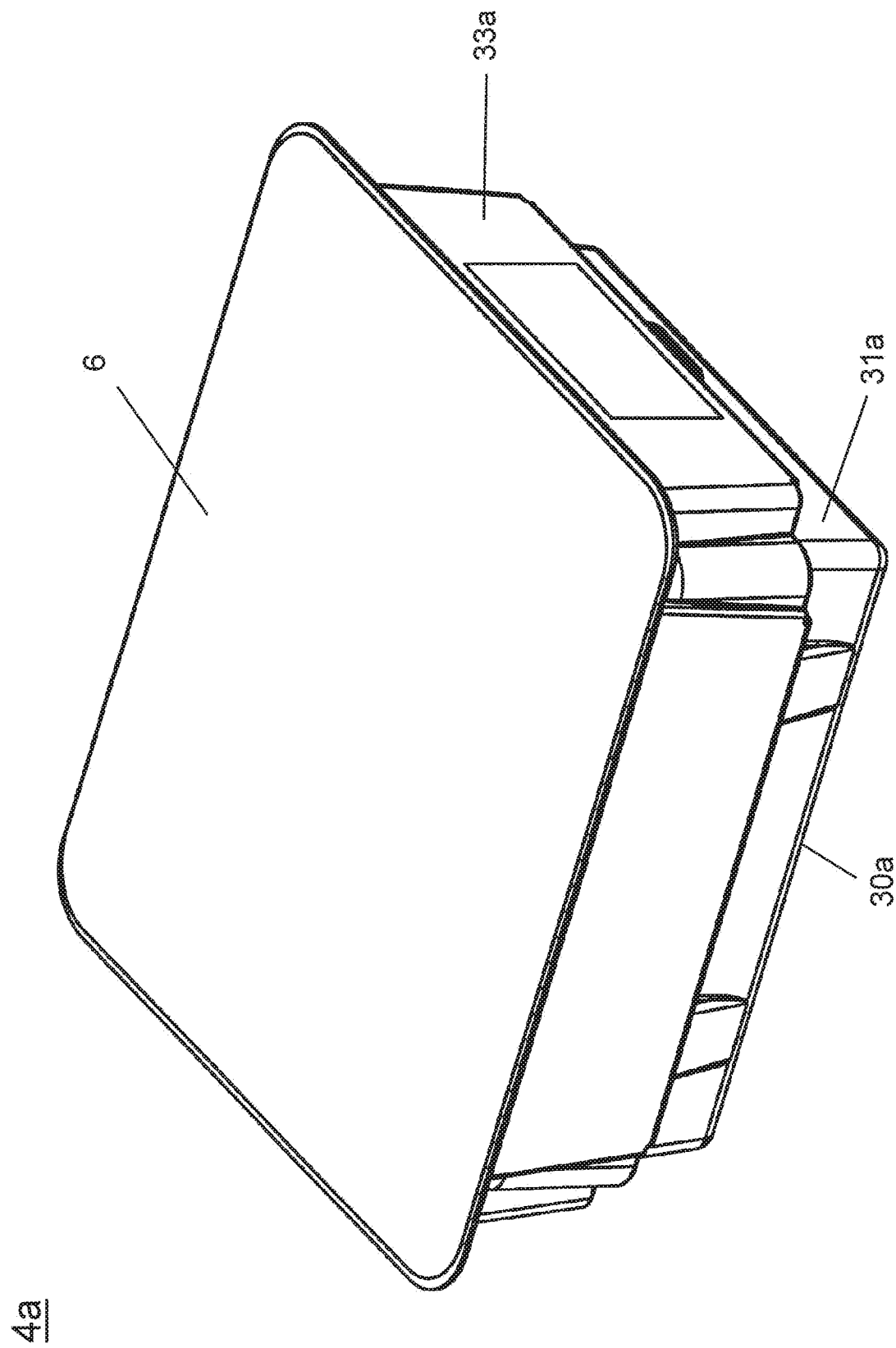

METHOD FOR CLOSING CARTRIDGES, SUPPORTING STRUCTURE FOR SUPPORTING CARTRIDGE CLOSURES AND TRANSPORT OR PACKAGING CONTAINER

The present application is a division of and claims priority under 35 U.S.C. § 120 to co-pending U.S. application Ser. No. 15/564,305, filed 4 Oct. 2017, which is a U.S. National Stage Application based on and claiming benefit and priority under 35 U.S.C. § 371 of International Application No. PCT/IN2016/000099, filed 18 Apr. 2016, which in turn claims benefit of and priority to PCT/IN2015/000394 filed 16 Oct. 2015 and which in turn claims benefit of and priority to Indian Application No. 1590/MUM/2015 filed 17 Apr. 2015, the entireties of which are hereby incorporated herein by reference.

FIELD OF INVENTION

The present invention relates in general to the processing of a batch of sealed cartridges, particularly of pre-crimped cartridges, for use in pharmaceutical, medical or cosmetic applications and relates in particular to a supporting structure (also named nest) provided for holding closures, such as elastic plugs or plunger stoppers, for use in a process for closing or stoppering cartridges. Further aspects of the present invention relate to a nest and tub assembly accommodating such closures, which can be directly fed on existing filling and stoppering machine set-ups for processing sealed prefillable syringe barrels. Further aspects of the present invention relate to a stoppering process and to an integrated filling and stoppering process for processing sealed prefillable syringe barrels.

BACKGROUND OF INVENTION

Conventionally presterilized prefillable syringe barrels are supplied in tub and nest assemblies that are hermetically sealed to the environment to pharmaceutical customers, who then fill medicine into the presterilized nested syringe barrels under sterile conditions using filling and stoppering machines. In the market there are three types of filling and stoppering machines available, namely 1) manual machines, 2) semi-automatic machines and 3) fully automatic machines.

There is one tub and nest format available in the market for pre-crimped cartridges but there are lots of disadvantages to use this existing tube and nest format with existing as well as new filling and stoppering machines because this tub and nest format requires complete setting change from infeed to outfeed for accommodating different height level of cartridge into the nest. Moreover a complete replacement of filling carriers is required for maintaining the height between the filling nozzles and the cartridge top level. Further the drawback of two different change parts needs separate validation study as per GMP (Good Manufacturing Practice) guidelines requirements. If one tries to fill the pre-crimped cartridge nest available in the market on the same machine without changing the machine height setting accidents will happen which may cause damage to the filling nozzles or glass cartridges may get broken because the height difference between the filling nozzles and the pre-crimped cartridges is too small.

These disadvantages similarly hold 1) for manual filling and stoppering machines, which are operated electrically and pneumatically and where the processes are triggered by an operator, 2) for semi-automatic filling and stoppering machines, which are operated electrically, electronically and pneumatically and where the operator has to remove the outer bag of the tub and nest assembly and then a top lid from the tub along with an inner sheet, and 3) for fully automatic filling and stoppering machines, which are operated electrically, electronically and pneumatically and where whole packets are inserted into the filling and stoppering machine one by one, the machine will automatically remove the outer bag and then remove the top lid from the tub by means of an automatic peeling off unit, then the inner sheet of the tub and nest assembly will be removed automatically and the machine will then automatically pick up the nests by means of a vacuum cup and place them onto transport carriers, which are then moved towards the filling station nozzles for the medicine filling process.

The currently available tub and nest assemblies in the market require the replacement of filling carriers for maintaining an accurate height difference between the filling nozzles and the cartridge top levels. Further after replacement of the filling carriers the replacement parts require separate validation studies as per GMP guidelines requirements. If the tub and nest assemblies available in the market are directly fed for filling of pre-crimped cartridges on the same machine without any alterations in the filling machines then the filling nozzles can be damaged or glass cartridges can be broken because the height difference between the filling nozzles and the pre-crimped cartridges is too small. All the above activities will incur higher costs and also additional time will be required to change the parts resulting in production losses. Further all fully automatic machines and new separate change parts are very expensive.

The above drawbacks are overcome by a supporting structure for supporting a plurality of sealed cartridges for use in pharmaceutical, medical or cosmetic applications, by a transport or packaging container accommodating such a supporting structure and by a process for processing a batch of sealed cartridges using such a supporting structure as disclosed in Indian patent application no. 1590/MUM/2015 and PCT-application no. PCTIN2015000394 of the Applicant, the whole content of which is hereby incorporated for reference.

US 2013/0161225 A1 discloses a packaging unit for the transport and processing of syringe bodies, comprising a tray which can retain a plurality of syringe bodies in a suspended vertical position, and a cover which can cover the tray. The cover comprises at least two flanks which can embrace the tray. According to an embodiment openings are provided in the upper wall of the cover which permit the circulation of steam or gas during a sterilization process. According to a further embodiment, these openings are placed above openings in the containers, and thus permit filling and/or plugging of the containers.

Conventionally, cartridges are closed by feeding closures, such as elastic plugs or plunger stoppers, individually to a closing machine and closing the cartridges individually, as disclosed e.g. in US 2014/0069062 A1. This often requires removal of the cartridges from a carrier after filling and re-inserting the cartridges after closing into the carrier again, as disclosed e.g. in U.S. Pat. No. 8,978,344 B2.

Typically the closures are singulated using vibratory bowls and transported using vibratory chutes. The vibratory bowl and chutes contact the stoppers, the surfaces of which will eventually be in direct contact with the product inside the container. To address this problem, it is generally considered necessary to steam sterilize the vibratory bowls and chutes. However, is practically impossible to transfer the stopper bowl and chutes aseptically from the sterilizing autoclave to the processing environment.

US 2012/0248057 A1 discloses a capping system method for sealing pharmaceutical vials. A plurality of vials are disposed upright in a tub, which also accommodates a respective closure assembly for each vial comprising a preassembled elastomeric stopper and a retainer member. Each closure member is placed on the neck of its associated vial so that a portion of the stopper partially closes the opening of the vial. Thereafter a force is applied to each of the closure assemblies to cause the retainer members to snap-fit on the flanged neck of their associated vial so that portions of their associated stopper seal the opening in their associated vial. This approach makes it easier to seal the vials under aseptic conditions.

A process for filling pharmaceutical containers that uses a similar capping system is disclosed in WO 2015/023924 A2. The process uses nests that are configured to allow multiple closures and containers to be simultaneously aligned concentrically, and closed simultaneously. Spring-loaded retaining structures on the closure nest allow it to releasably retain multiple closures above the corresponding multiple containers. The retaining structures used are, however, still complicated and it is not easy to use this approach in the existing machinery of pharmaceutical fillers.

SUMMARY OF INVENTION

According to the present invention there is provided a stoppering process or an integrated filling and stoppering process for processing sealed prefillable syringe barrels using a supporting structure for holding a plurality of closures. According to a further related aspect of the present invention there is provided a supporting structure for holding a plurality of closures (nest for closures), such as elastic plugs or plunger stoppers, for use in the process for closing or stoppering cartridges. According to a related further aspect of the present invention there is provided a transport or packaging container (nest and tub assembly) accommodating at least one nest for closures configured so that the nest accommodating the closures can be directly fed on existing filling and stoppering machine set-ups for processing sealed prefillable syringe barrels.

A supporting structure for closures according to the present invention, for use in the stoppering process or an integrated filling and stoppering process, is configured for releasably supporting a plurality of closures, which have a cylindrical shape, consist of a resilient material and are for use for closing cartridges for use in pharmaceutical, medical or cosmetic applications. The supporting structure for closures comprises a planar supporting plate having a plurality of tubular receptacles for accommodating the closures at least partially, for concurrently supporting a plurality of closures at the supporting plate. According to the present invention the receptacles are formed by circumferential side walls disposed in a regular arrangement at the supporting plate and protruding from the supporting plate, wherein the receptacles are configured for accommodating the closures at least partially.

The supporting structure for closures allows to releasably hold a plurality of closures exactly in the same two-dimensional arrangement as a supporting structure for cartridges disclosed in Indian patent application no. 1590/MUM/2015 and PCT-application no. PCTIN2015000394 of the Applicant. This simplifies a process for closing the cartridges significantly, because this process only requires disposing the supporting structure for closures above the supporting structure for cartridges in an environment with reduced pressure so that the receptacles of the supporting structure for closures are aligned with their associated receptacles of the supporting structure for cartridges, and pushing the closures downward out of the receptacles of the supporting structure for closures and into the filling openings at the upper ends of the cartridges while the cartridges are accommodated in the receptacles of the supporting structure for cartridges.

As the supporting structure according to the present invention can be easily accommodated and stored or transported in a transport container (tub), the present invention enables using the existing tube and nest format widely used in the market with existing as well as new filling and stoppering machines. Furthermore, the supporting structure according to the present invention can be used to efficiently store and supply a plurality of closures in a predetermined geometrical arrangement under sterile conditions, using the tube and nest format widely used in the market.

The receptacles may accommodate the closures fully or only partially, depending on the circumstances of the further processing of the closures and cartridges. The supporting plate is preferably made of a plastic material, e.g. by plastic injection molding, and offers sufficient strength, stiffness and mechanical stability, although these requirements are usually easy to fulfill, because the closures to be accommodated are light-weight and only small forces are usually exerted on the supporting plate during further processing.

The closures may be accommodated in the receptacles solely by friction. As the closures are made of an elastic, resilient material, inserting the closures into the receptacles might involve imposing a slight elastic deformation of the closures so that the closures abut resiliently against the circumferential side walls of the receptacles. As the closures are light-weight, a reliably accommodation of the closures would usually require only a small degree of deformation of the closures, which corresponds to small forces required only for inserting or removing the closures into and out of the receptacles. As closures for cartridges, such as plunger stoppers, usually have several annular bulges on their outer circumference, this slight elastic deformation would usually occur only in the region of these annular bulges. Thus, the side walls of the receptacles are preferably straight sidewalls defining cylindrical receptacles that are not tapered.

For more reliably accommodating the closures in the receptacles, according to a further embodiment the receptacles comprise retaining structures that releasably engage with the closures for retaining the closures in the receptacles. Preferably the retaining structures engage with the closures in a form-fitting manner. This form-fitting engagement may be implemented at the upper and bottom ends of the closures, or at any other suitable positions, such as at the bottom ends and at central portions of the closures, which might be concavely curved for example in the case of plunger stoppers. For this purpose, the retaining structure may slightly protrude into the interior of the receptacles to retain the closures.

According to a further embodiment the protrusions are formed on the inner sides of the circumferential side walls of the receptacles, which may be easily accomplished by integrally forming the protrusions with the side-walls of the receptacles, e.g. by plastic injection molding.

According to a further embodiment the protrusions may be configured to mate to the outer contour of the closures. If e.g. the outer contour of the closures is undulated, the protrusions may at least be partially undulated in correspondence to the outer contour of the closures.

According to a further embodiment the protrusions may be formed at equal angular distances along the inner sides of the circumferential side walls of the receptacles, e.g. as small spot-like protrusions. According to an alternative embodiment, however, the protrusions may also be formed as circumferential protrusions on the inner sides of the circumferential side walls of the receptacles.

According to a further embodiment the receptacles may comprise upper retaining structures formed at or near an upper end of the receptacles and bottom retaining structures formed at a bottom end of the receptacles, wherein the distance between the respective upper and bottom retaining structures may be equal to the axial length of the closures so that the closures are reliably fixed in both axial directions in the receptacles. The closures may even rest on these retaining structures thus enabling a substantially frictionless accommodation of the closures in the receptacles and removing the closures out of the receptacles with small forces only. According to a further embodiment, however, this distance may also be smaller, e.g. if one of the retaining structures engages with a portions of the closures in a form-fitting manner.

According to a particularly preferred embodiment the upper retaining structures may be formed as convexly curved protrusions protruding from the inner sides of the circumferential side walls of the receptacles which enables an insertion of the closures into the receptacles with small forces and a slight elastic deformation only, whereas the bottom retaining structures may be formed as hook-like protrusions protruding from the inner sides of the circumferential side walls of the receptacles, which enables to push down the closures out of the receptacles simultaneously because the timing when the retaining forces are overcome by a pushing force of a stoppering machine can be precisely adjusted, e.g. by means of the geometric shape of the bottom retaining structures, their material and strength.

According to a particularly preferred embodiment the bottom retaining structures may beveled on an upper and/or lower side thereof. While the bevel on the upper side eases the pushing down of the closures out of the receptacles during a stoppering process, the bevel on the lower side may helpful if the receptacles are directly supported on upper ends of the cartridges during the stoppering process, because the bevels on the lower sides may then snuggle to these upper ends and peak forces or tension may thus be avoided, particularly if the bottom retaining structures are made of a resilient plastic material.

According to a further related aspect of the present invention there is provided a transport or packaging container for accommodating a plurality of closures for closing cartridges for use in pharmaceutical, medical or cosmetic applications, wherein the transport or packaging container is box-shaped and comprises: a bottom, which is closed or sealed by a seal, upstanding lower side-walls extending essentially perpendicularly from said bottom, a circumferential supporting step extending horizontally from said side-walls, upper side-walls extending upward from said supporting step, and a circumferential flange formed at upper ends of the upper side-walls. According to the present invention at least one supporting structure for closures as disclosed in the present application is accommodated in the transport or packaging container, wherein the plurality of closures are accommodated in the receptacles of the at least one supporting structure for closures.

The transport or packaging container for closures enables the storage and transport of a plurality of closures in exactly the same format as the existing tube and nest format widely used in the market so that it may be used easily with existing as well as new filling and stoppering machines without the necessity of changing the whole setup thereof.

According to a further embodiment the edge of the bottommost planar supporting plate of the supporting structure for closures may be supported directly on the circumferential supporting step or the transport or packaging container.

According to a further embodiment a plurality of supporting structures for closures may be accommodated together inside the transport or packaging container stacked one above the other. For this purpose, spacers might be provided on the bottom sides of the supporting plates. However, this is usually not required, because usually the bottom ends of the receptacles of an upper closure nest may rest directly on the bottom surface of another closure nest, because the outer diameter of the receptacles is larger than the inner diameter of the receptacles, so that the receptacles of the upper closure nest cannot enter the receptacles of another closure nest. For this purpose, it might be of advantage if the upper ends of the closures are disposed at a certain minimum distance to the upper ends of the receptacles.

According to a further embodiment the transport or packaging container is closed or sealed by a protective foil against the environment, the protective foil being bonded to the circumferential flange. The protective foil may be impermeable to gas, thus implementing completely sterile conditions during storage and transport of the closures.

According to a particularly preferred embodiment the protective foil may be a gas-permeable plastic film enabling a sterilization of the interior of the transport or packaging container through the protective foil by a flow of a sterilization gas, such as ethylene oxide. Particularly the protective foil may be made of a web of synthetic fibers such as polypropylene fibers (PP) or a Tyvek® protective film for this purpose.

According to a further related aspect of the present invention there is provided a method for closing a plurality of cartridges for use in pharmaceutical, medical or cosmetic applications, said cartridges having an upper end and a bottom end opposite to the upper end, a cylindrical body of a first outer diameter with a filling opening at the upper end, and a shoulder portion at the bottom end with a secondary opening which is sealed by a seal, a predetermined axial length being defined between the upper end and the bottom end, said method comprising: providing a supporting structure for closures as disclosed in the present application accommodating a plurality of closures in the receptacles in a regular arrangement; providing a supporting structure for cartridges as disclosed in Indian patent application no. 1590/MUM/2015 and PCT-application no. PCTIN2015000394 of the Applicant, accommodating a plurality of cartridges in the same regular arrangement as in the supporting structure for closures; disposing the supporting structure for closures above the supporting structure for cartridges in an environment with reduced pressure so that the receptacles of the supporting structure for closures are aligned with the receptacles of the supporting structure for cartridges; and pushing the closures simultaneously downward out of the receptacles of the supporting structure for closures and into the filling openings at the upper ends of the cartridges while the cartridges are accommodated in the receptacles of the supporting structure for cartridges.

The nest accommodating the closures can be directly fed on existing filling and stoppering machine set-ups for processing sealed prefillable syringe barrels. The method according to the present invention can be implemented easily for cartridges of different lengths, because this requires just an adjustment of the distance between the supporting structure for closures and the supporting structure for cartridges, which can be accomplished by a simple vertical adjustment of either supporting structure, which does not change the exact alignment of the receptacles of both supporting structures.

According to a further embodiment the supporting structure for cartridges is held by a bottom holding frame, whereas the supporting structure for closures is held by an upper holding frame, wherein the bottom holding frame and the upper holding frame are disposed at a fixed spacing and aligned with each other by alignment devices. For this purpose one of the holding frames may be provided with alignment devices, such as protrusions, rods or the like, that cooperate with corresponding alignment devices, such as holes or recesses, provided on the other holding frame. Thus, an exact, reliable alignment of all receptacles of the supporting structures can be accomplished easily.

According to a further embodiment the upper holding frame may be disposed at such a distance to the bottom holding frame that bottom ends of the receptacles of the upper holding frame or bottom ends of the receptacles of the supporting structure for closures held by the upper holding frame are in direct contact with the upper ends of the cartridges accommodated in the receptacles of the supporting structure for cartridges so that the closures are directly guided into the open upper ends of the cartridges if pushed down out of the receptacles of the supporting structure for closures.

In this method, the supporting structures for closures and/or the supporting structures for cartridges may be supplied under sterile conditions, e.g. to a pharmaceutical filler, in transport and packaging containers as outlined in the following in more detail.

Of course, the method according to the present invention may involve additional processing steps, particularly a step of filling the plurality of cartridges with a pharmaceutical, medical or cosmetic product, which can be performed in any suitable sequence, particularly row-wise or simultaneously for all cartridges supported by a supporting structure.

According to a further embodiment this step of filling the plurality of cartridges with the pharmaceutical, medical or cosmetic product may be performed while the supporting structure for cartridges is held in the same bottom holding frame used during stoppering.

The above aspects of the present invention are thus closely related to a supporting structure for supporting a plurality of sealed cartridges for use in pharmaceutical, medical or cosmetic applications as disclosed in Indian patent application no. 1590/MUM/2015 and PCT-application no. PCTIN2015000394 of the Applicant, said cartridges having an upper end and a bottom end opposite to the upper end, a cylindrical body of a first outer diameter with a filling opening at the upper end, and a shoulder portion at the bottom end with a secondary opening which is sealed by a seal, a predetermined axial length being defined between the upper end and the bottom end. The supporting structure comprises a planar supporting plate, and a plurality of tubular receptacles formed at the planar supporting plate in a regular arrangement and extending downward from a bottom side of the planar supporting plate for accommodating the sealed cartridges, wherein retaining protrusions are formed at the bottom ends of the receptacles protruding inward, and the axial length of the receptacles is smaller than the axial length of the sealed cartridges.

According to the present invention the retaining protrusions are mated with the shoulder portions of the sealed cartridges in such a manner that the shoulder portions of the sealed cartridges are supported on the retaining protrusions of the receptacles and that the upper ends of the sealed cartridges protrude from the upper ends of the receptacles at an upper side of the planar supporting plate, when the sealed cartridges are accommodated upside-down in the receptacles.

Because the seals of the cartridges at their bottom ends, which are susceptible to damage upon application of excessive forces, do not rest on a supporting surface the cartridges, once filled, may be stoppered (closed at their upper ends with rubber plugs, plungers or similar sealing members) without damaging the seals at the bottom ends. At the same time, the filling openings, which extend beyond the upper rims of the receptacles, are freely accessible for processing.

According to a further embodiment the receptacles are of cylindrical shape and a plurality of ribs are formed at equidistant angular spacing on inner circumferential side-walls of the receptacles, preferably at diametrically opposite positions thereof, wherein the ribs protrude radially inward from the inner circumferential side-walls of the receptacles for centering the sealed cartridges inside the receptacles. Thus, a reliable centering of the cartridges, a rattle-free storage inside the receptacles and a smooth, rattle-free insertion into and removal out of the receptacles may be accomplished. Further, forces exerted e.g. upon stoppering may be distributed more efficiently without deformation of the receptacles, thus ensuring a more precise centering and positioning of the cartridges inside the receptacles.

According to a further embodiment the retaining protrusions are formed as ring segments that protrude radially inward at the bottom ends of the receptacles and at equidistant angular spacing, preferably at diametrically opposite positions thereof, thus enabling a more uniform distribution of forces, particularly upon stoppering.

According to a further embodiment an outer diameter of the sealed cartridges at their sealed bottom ends is larger than the outer diameter at their shoulder portions but smaller than the first outer diameter. Further the thickness of the retaining protrusions in the axial direction may be smaller than the axial length of the sealed bottom ends so that the sealed bottom ends of the sealed cartridges extend through openings formed by the retaining protrusions at the bottom ends of the receptacles. The sealed bottom ends of the cartridges thus do not rest on any supporting surfaces but hang free in space, thereby reducing the risk of mechanical damage upon stoppering and related processing steps.

According to a further embodiment the supporting plate is formed of a plastic material and the side-walls of the receptacles and the retaining protrusions are formed unitary with the supporting plate, wherein the retaining protrusions are configured to sustain axial forces exerted onto the sealed cartridges of up to 1,000 N, preferably of up to 750 N and more preferably of up to 500 N.

According to a further embodiment the front ends of the retaining protrusions are wedge-shaped in correspondence with the outer contour of the shoulder portions of the sealed cartridges, thus enabling a more reliable and precise supporting of the shoulder portions and even less deformation of the retaining protrusions upon stoppering or related processing steps.

According to a further embodiment virtual connecting lines between the centers of directly adjacent receptacles respectively form a hexagon with a further receptacle disposed at a center of the respective hexagon, wherein the receptacles extend beyond the upper surface of the supporting plate and stiffening ribs protruding upward from the upper surface of the supporting plate are formed on the upper surface of the supporting plate so as to connect the circumferential side walls of the receptacles, for stiffening the supporting plate. Thus, a rather efficient stiffening of the supporting plate may be accomplished.

According to a further aspect of the present invention there is provided a transport or packaging container (tub) for accommodating a plurality of sealed cartridges for use in pharmaceutical, medical or cosmetic applications, wherein the transport or packaging container is box-shaped and comprises a bottom, which is closed or sealed by a seal, upstanding lower side-walls extending essentially perpendicularly from said bottom, a circumferential supporting step extending horizontally from said side-walls, upper side-walls extending upward from said supporting step and a circumferential flange formed at upper ends of the side-walls. A supporting structure (nest) as disclosed hereinafter in more detail is accommodated in the transport or packaging container and supports a plurality of sealed cartridges in the receptacles thereof. The nest rests directly on the supporting step of the tub. Thus, regardless of whether the cartridges are processed while being accommodated only in the nest or in a tub and nest assembly it can be ensured that the upper ends of all cartridges are on the same height level. Thus, a precise distance between the upper ends of the cartridges and the bottom ends of filling nozzles or the like can be ensured reliably, thus avoiding breakage or damage during processing of the cartridges.

According to a further embodiment the transport or packaging container further comprises a flexible lid sealed onto the circumferential flange of the transport or packaging container for sealing the transport or packaging container, preferably for hermetically sealing the inner volume of the transport or packaging container against the environment.

According to a further aspect of the present invention there is provided a process for processing a batch of sealed cartridges for use in pharmaceutical, medical or cosmetic applications, comprising the steps of: a) providing a supporting structure as disclosed hereinafter in more detail; b) disposing the sealed cartridges upside-down in the receptacles and with their upper ends protruding from the upper ends of the receptacles at an upper side of the planar supporting plate so that the shoulder portions of the sealed cartridges are supported on the retaining protrusions of the receptacles and the upper ends of the sealed cartridges are disposed at the same height level; c) feeding the supporting structure with the sealed cartridges to a processing station; and d) processing the sealed cartridges at their upper ends at the processing station while being supported by the supporting structure.

According to a further embodiment step d) comprises one or more of the following: filling the sealed cartridges via the filling openings at the upper ends; stoppering the sealed cartridges at their upper ends using rubber stoppers; pre gassing and post gassing.

According to a further embodiment the process further comprises: disposing the supporting structure in a frame-like holding table; feeding the supporting structure together with the sealed cartridges to the processing station while being supported by the frame-like holding table; and disposing the supporting structure with the sealed cartridges inside a box-shaped transport or packaging container after said step d), which comprises a bottom, upstanding lower side-walls extending essentially perpendicularly from said bottom, a circumferential supporting step extending horizontally from said side-walls, upper side-walls extending upward from said supporting step and a circumferential flange formed at upper ends of the side-walls so that the edge of the planar supporting plate of the supporting structure is supported on the circumferential supporting step of the transport or packaging container, the upper ends of the sealed cartridges do not protrude beyond the circumferential flange of the transport or packaging container, and the bottom ends of the sealed cartridges are disposed spaced apart from the bottom of the transport or packaging container.

According to a further embodiment the process further comprises: disposing the supporting structure with the sealed cartridges inside a box-shaped transport or packaging container, which comprises a bottom, upstanding lower side-walls extending essentially perpendicularly from said bottom, a circumferential supporting step extending horizontally from said side-walls, upper side-walls extending upward from said supporting step and a circumferential flange formed at upper ends of the side-walls so that the edge of the planar supporting plate of the supporting structure is supported on the circumferential supporting step, the upper ends of the sealed cartridges do not protrude beyond the circumferential flange of the transport or packaging container, and the bottom ends of the sealed cartridges are disposed spaced apart from the bottom of the transport or packaging container; wherein step c) further comprises: disposing the transport or packaging container in a frame-like holding table so that the supporting step of the transport or packaging container is supported on an upper side of the frame-like holding table and that the upper ends of the sealed cartridges are disposed at the same height level; and feeding the frame-like holding table together with the transport or packaging container, the supporting structure accommodated therein and the sealed cartridges to the processing station.

According to a further embodiment the transport or packaging container is sealed with a flexible lid.

According to a further embodiment of the process the sealed cartridges are pre-crimped cartridges.

OVERVIEW ON DRAWINGS

Hereinafter, the present invention will be disclosed in exemplary manner and with reference to the drawings, wherein.

Figure 1:
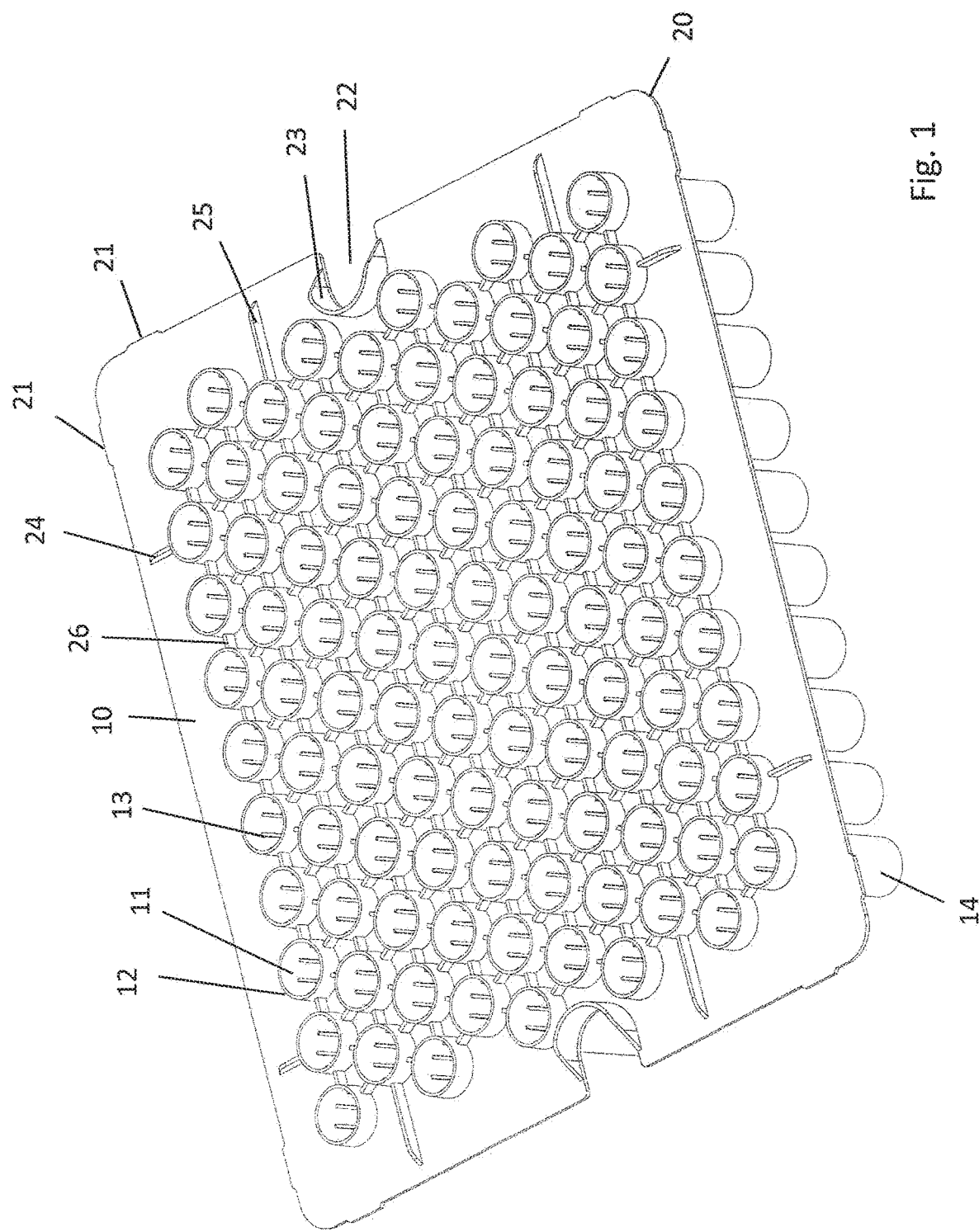
FIG. 1 is a perspective top view of a supporting structure for cartridges for use in a method according to the present invention.
Figure 5:
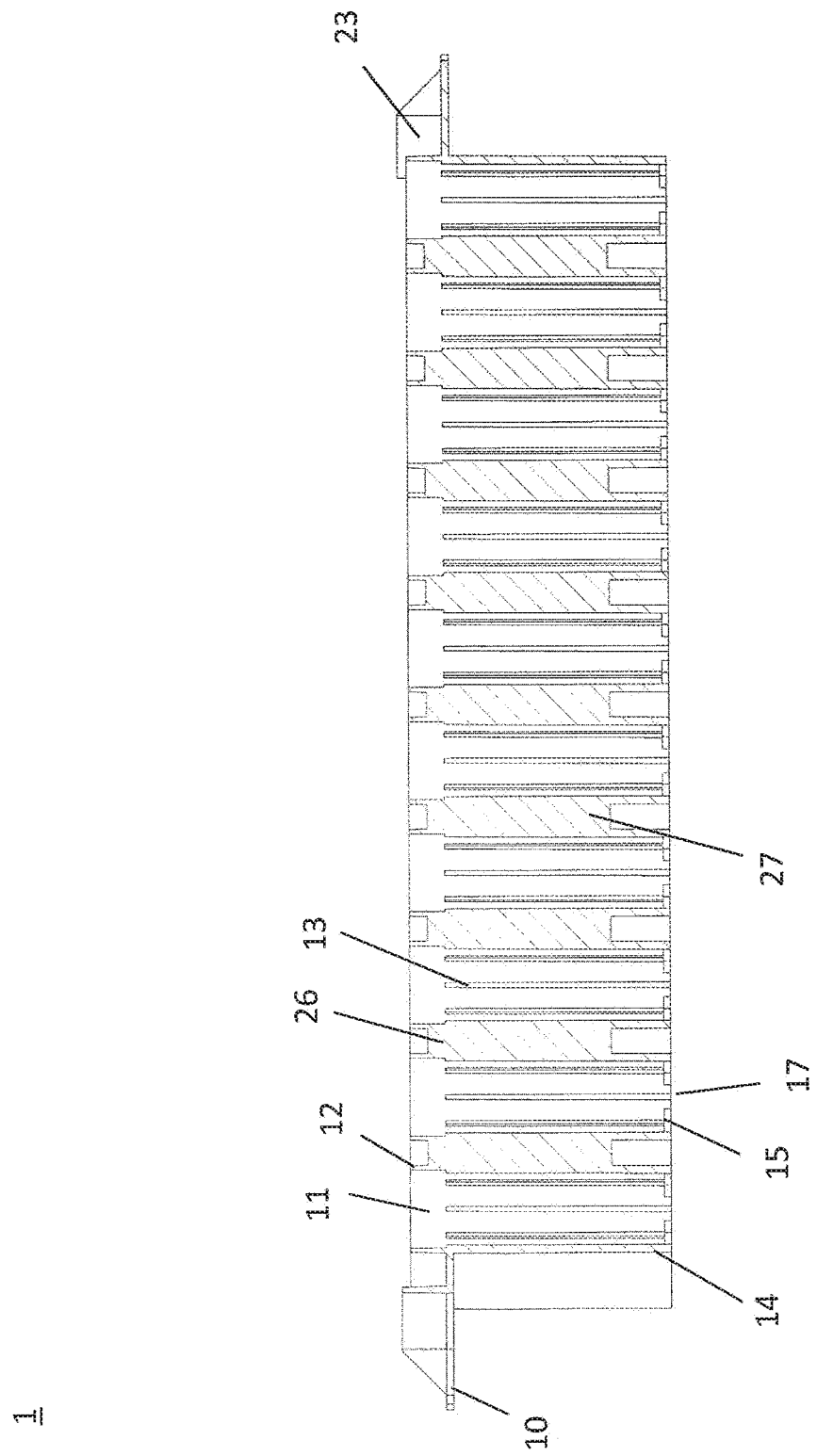
FIG. 5 is a schematic cross-section of the supporting structure of FIG. 1 without cartridges.
Figure 6A:
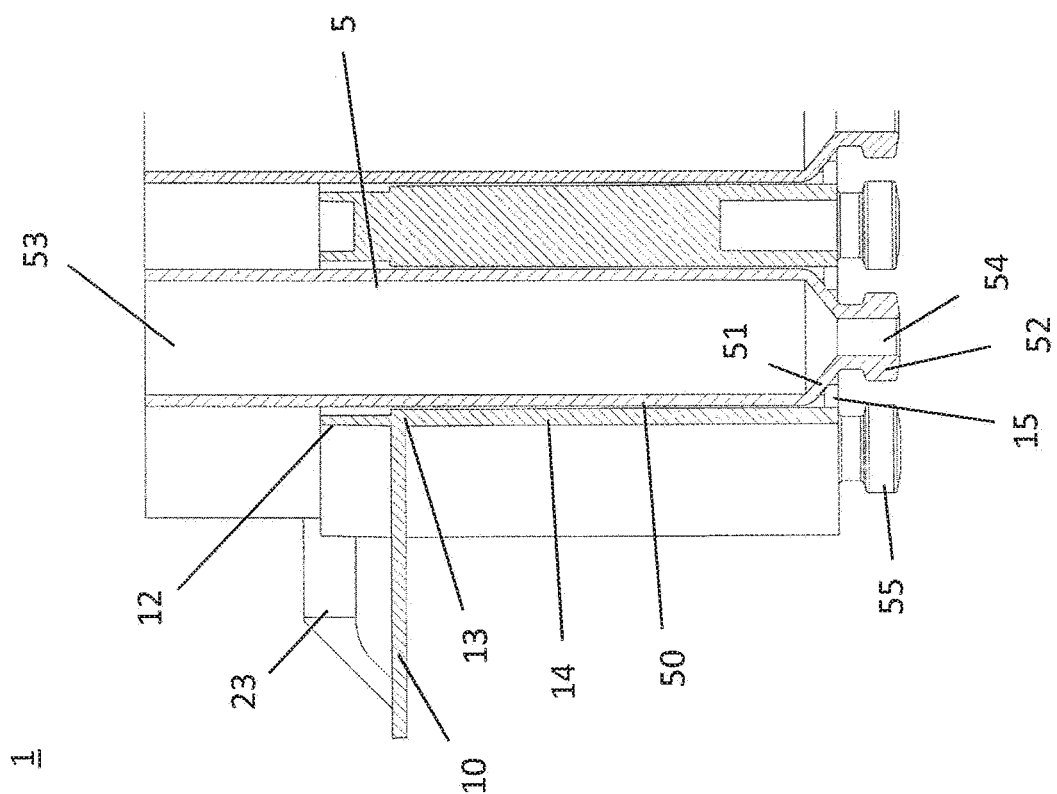
Figure 6B:
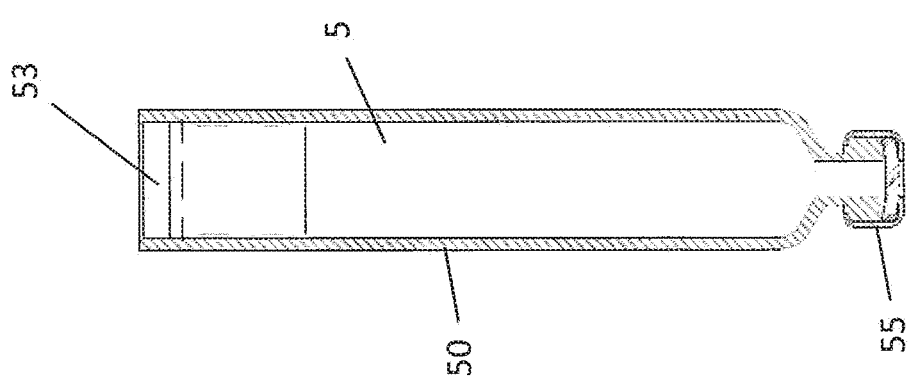
Figure 7:
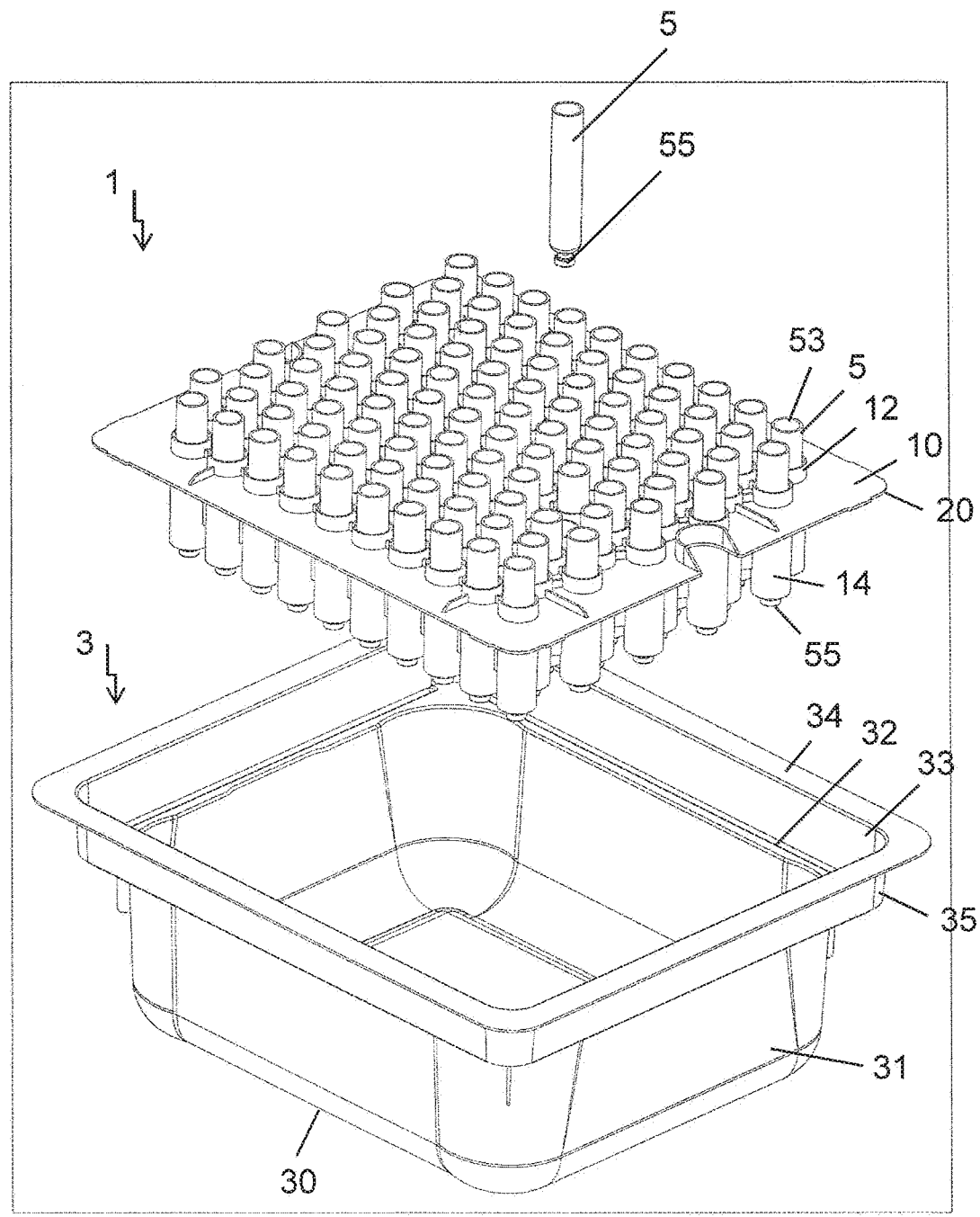
Figure 8:
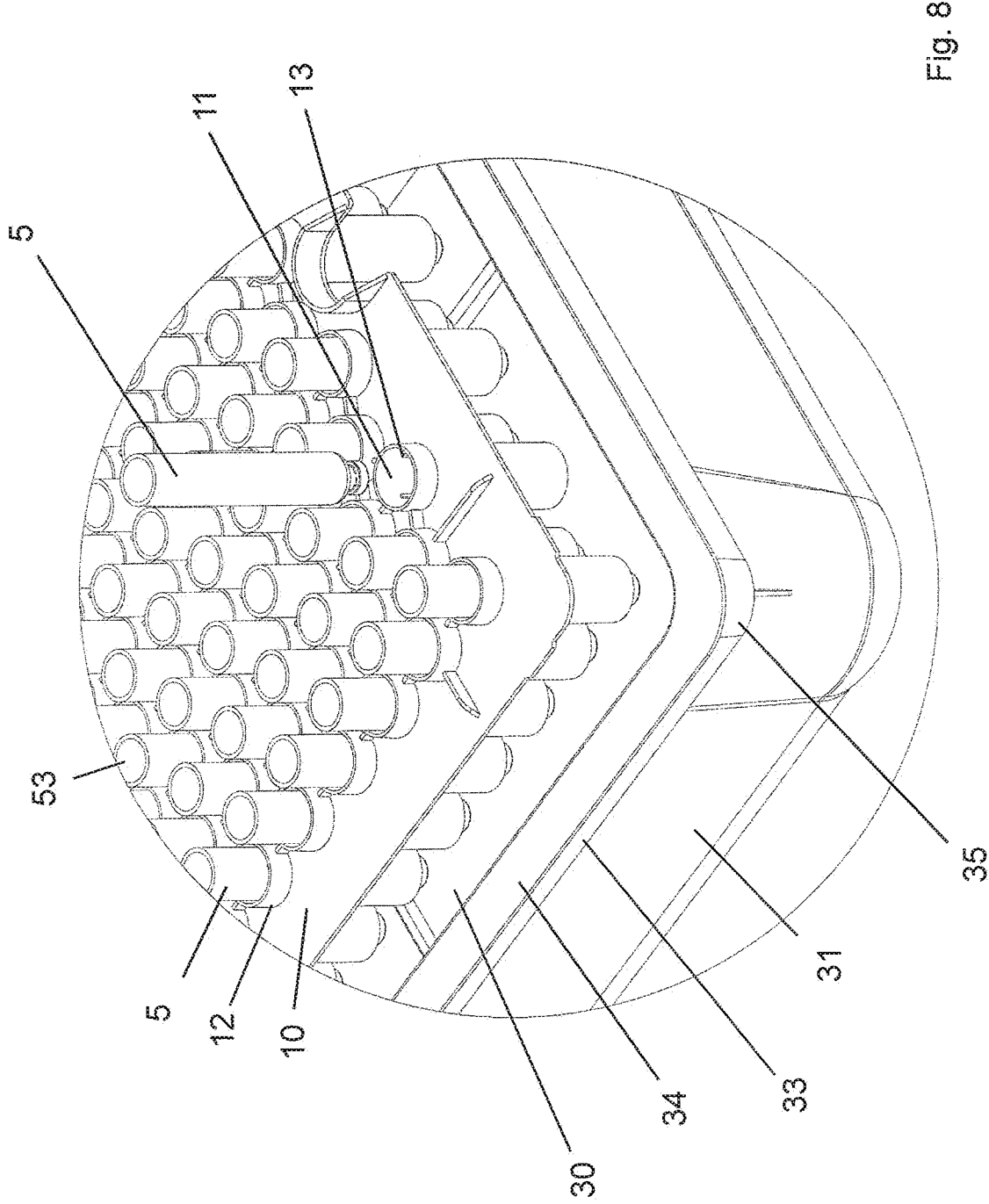
Figure 9:
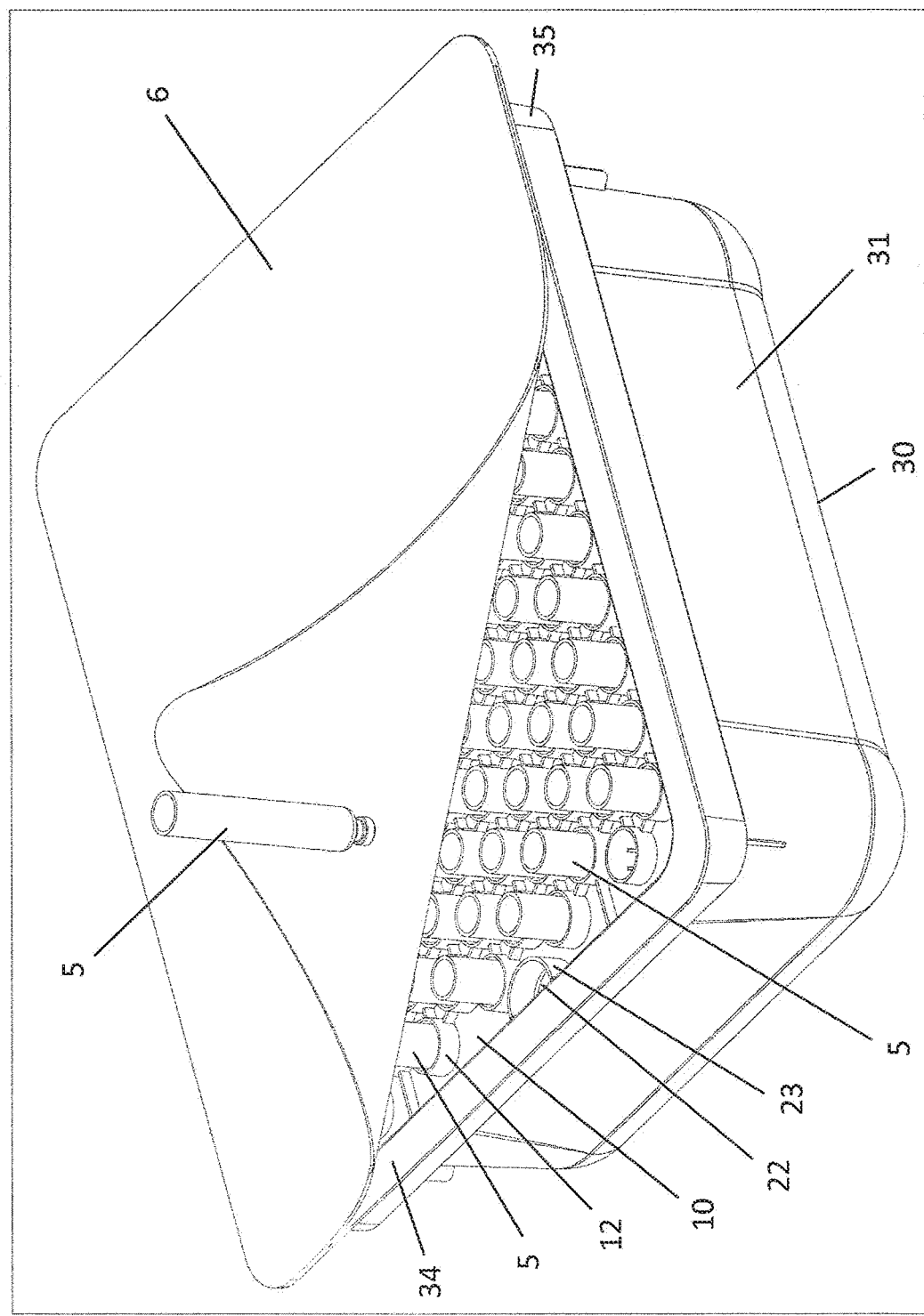
Figure 10:
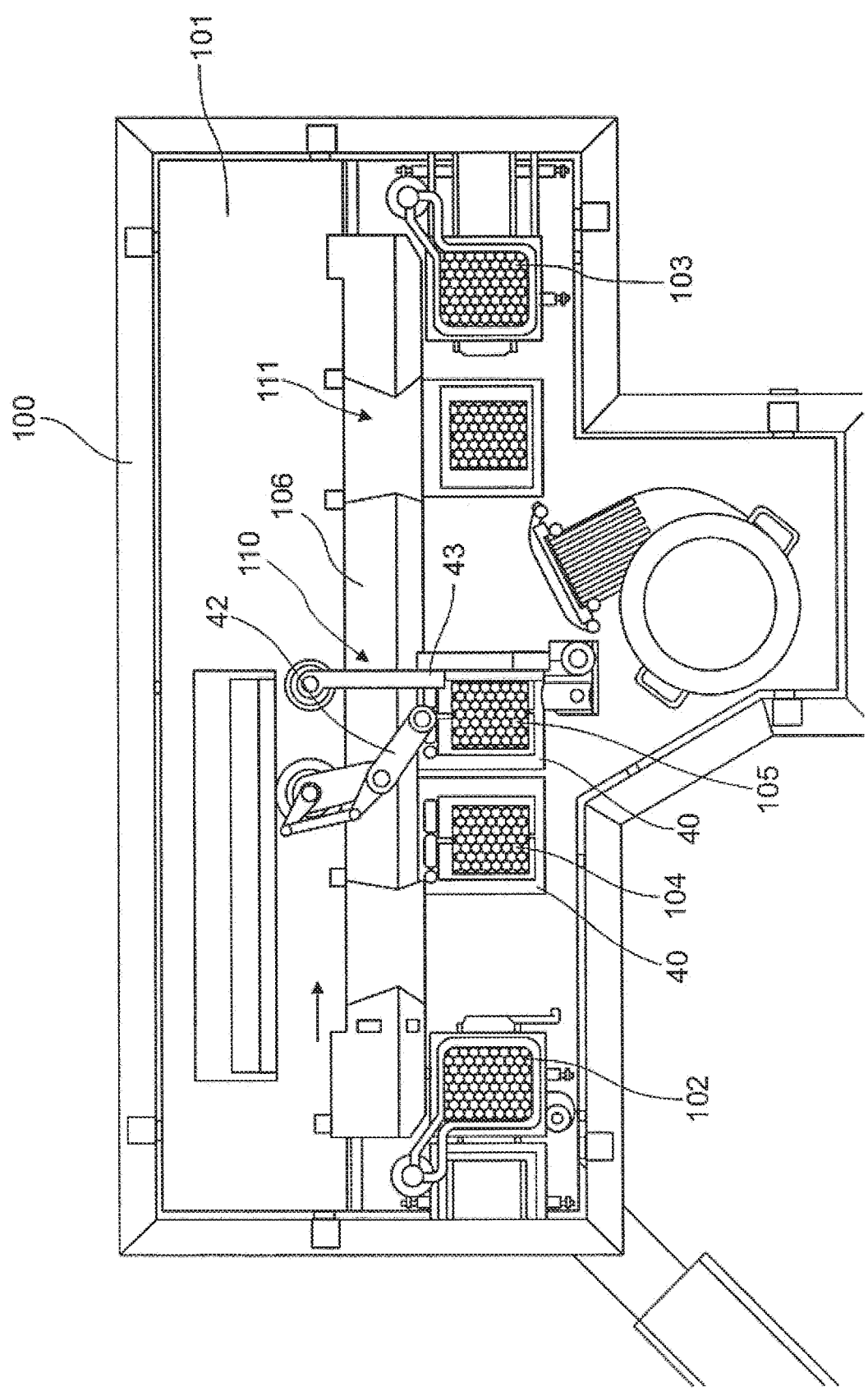
Figure 12A:
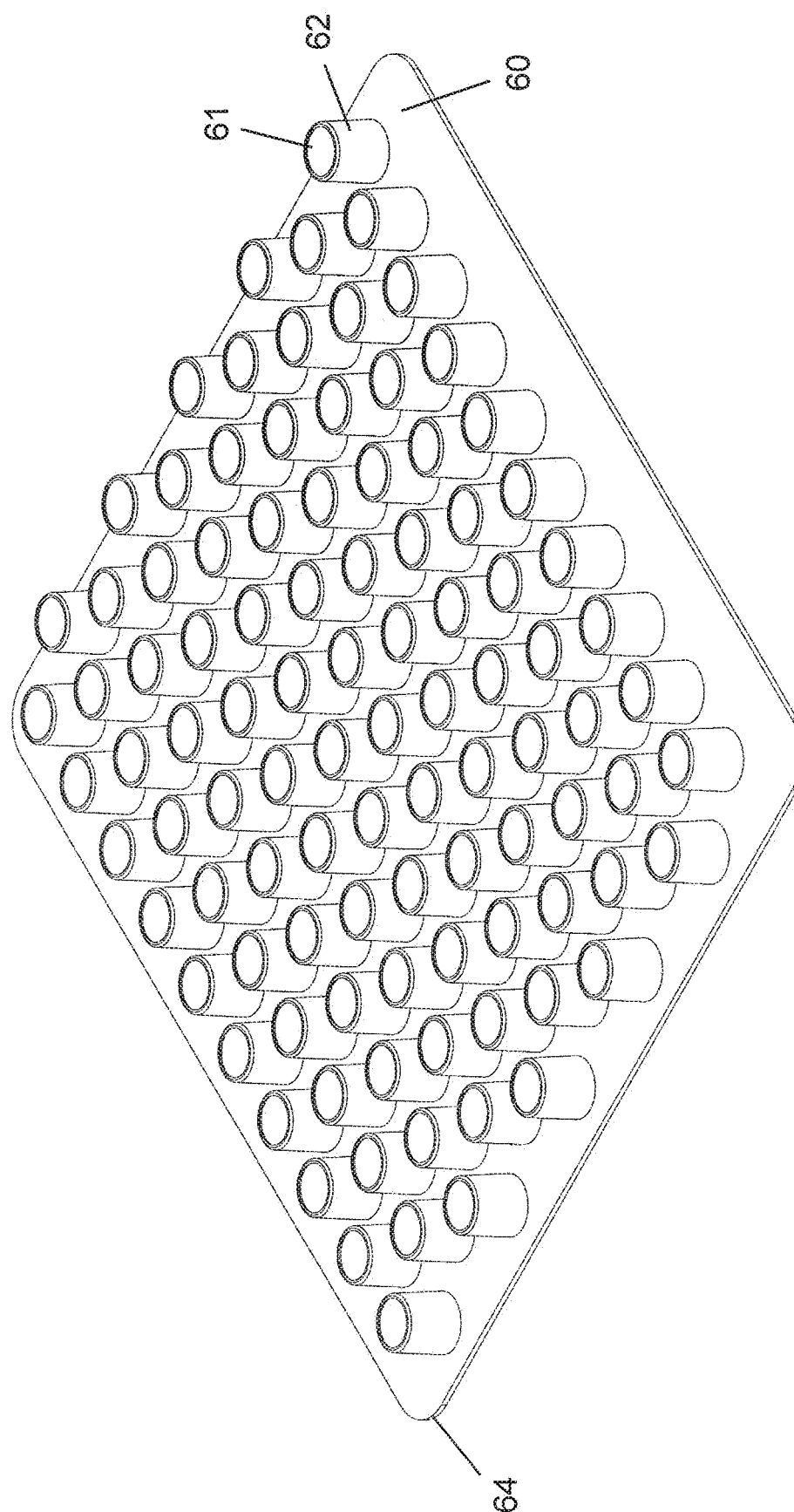
Figure 12B:
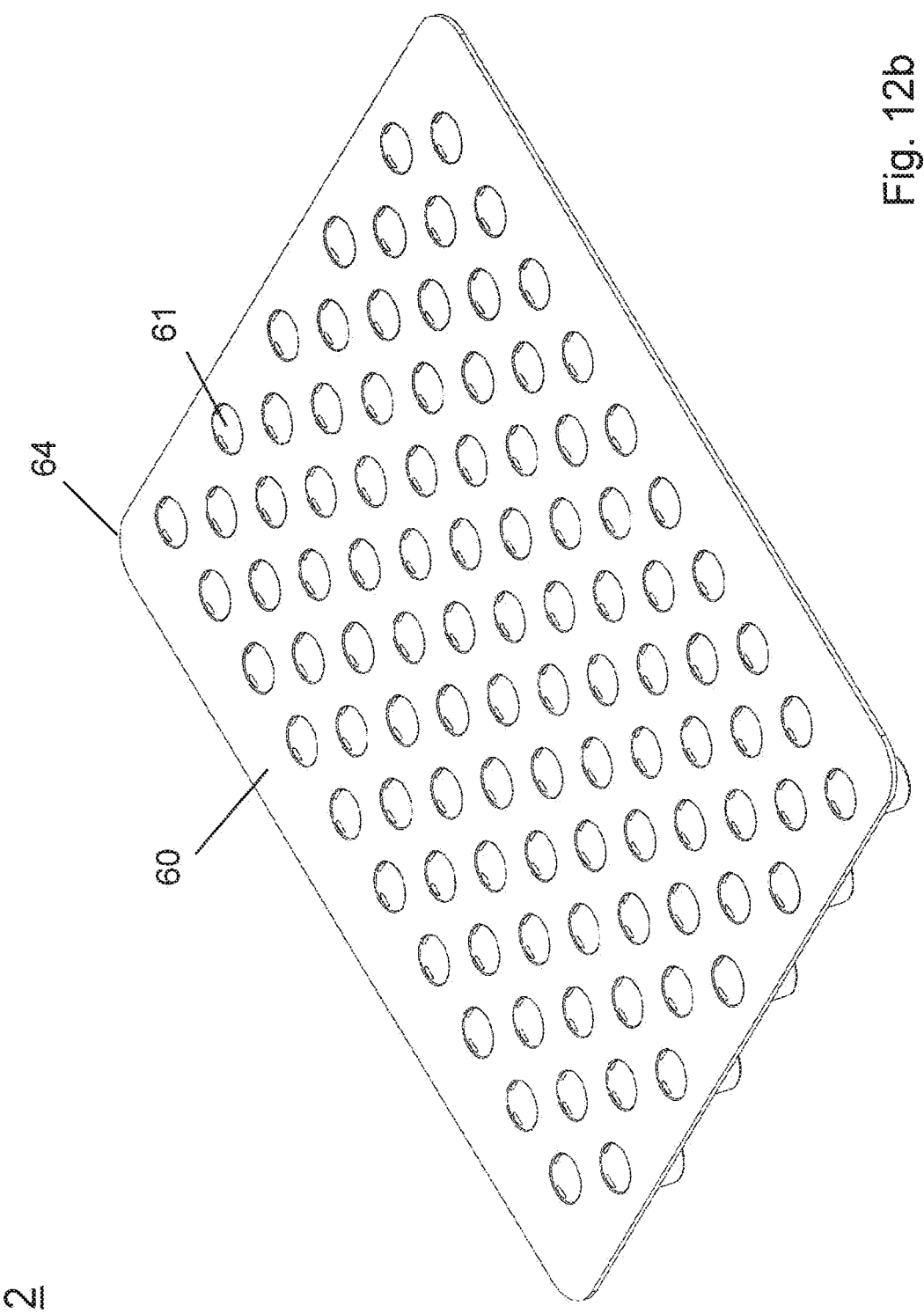
Figure 12D:
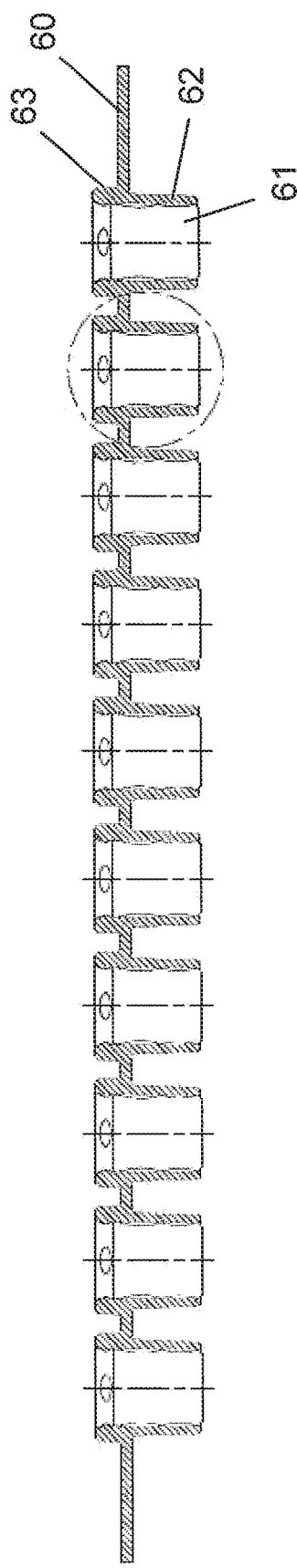
Figure 12E:
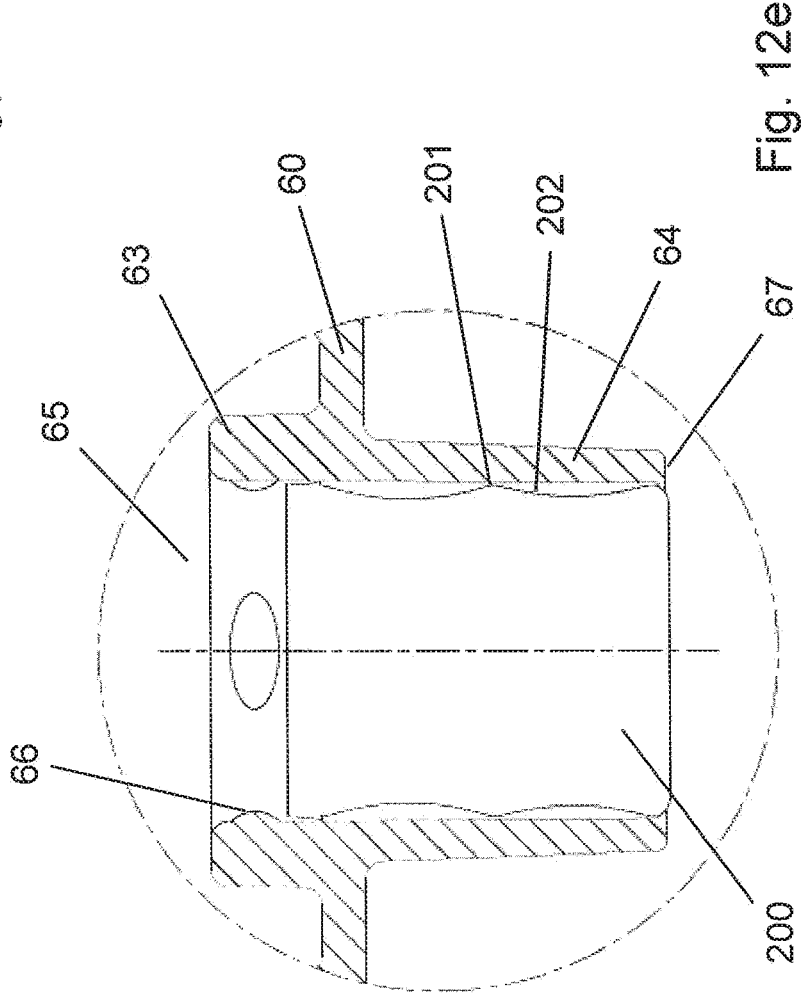
Figure 14A:
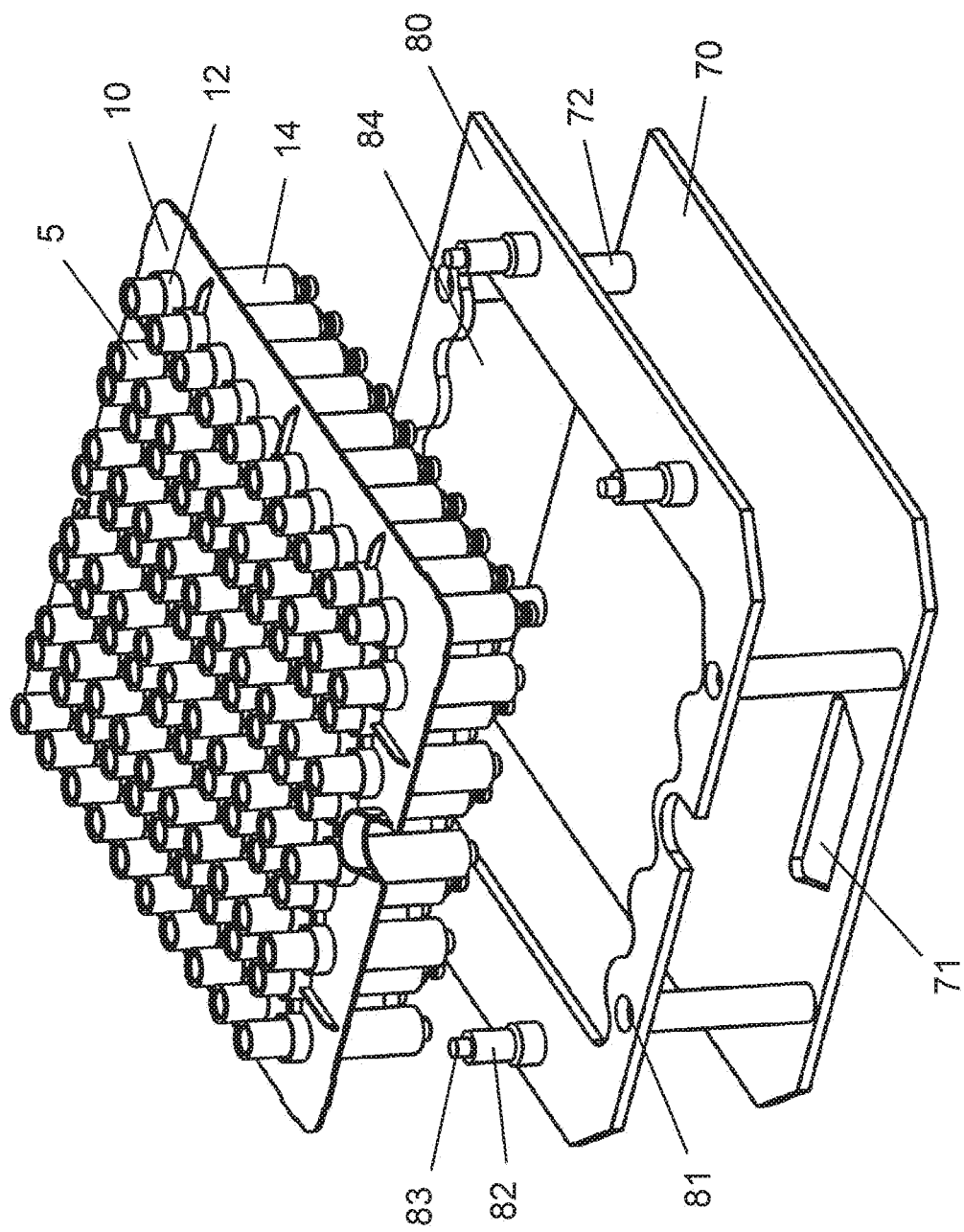
Figure 14B:
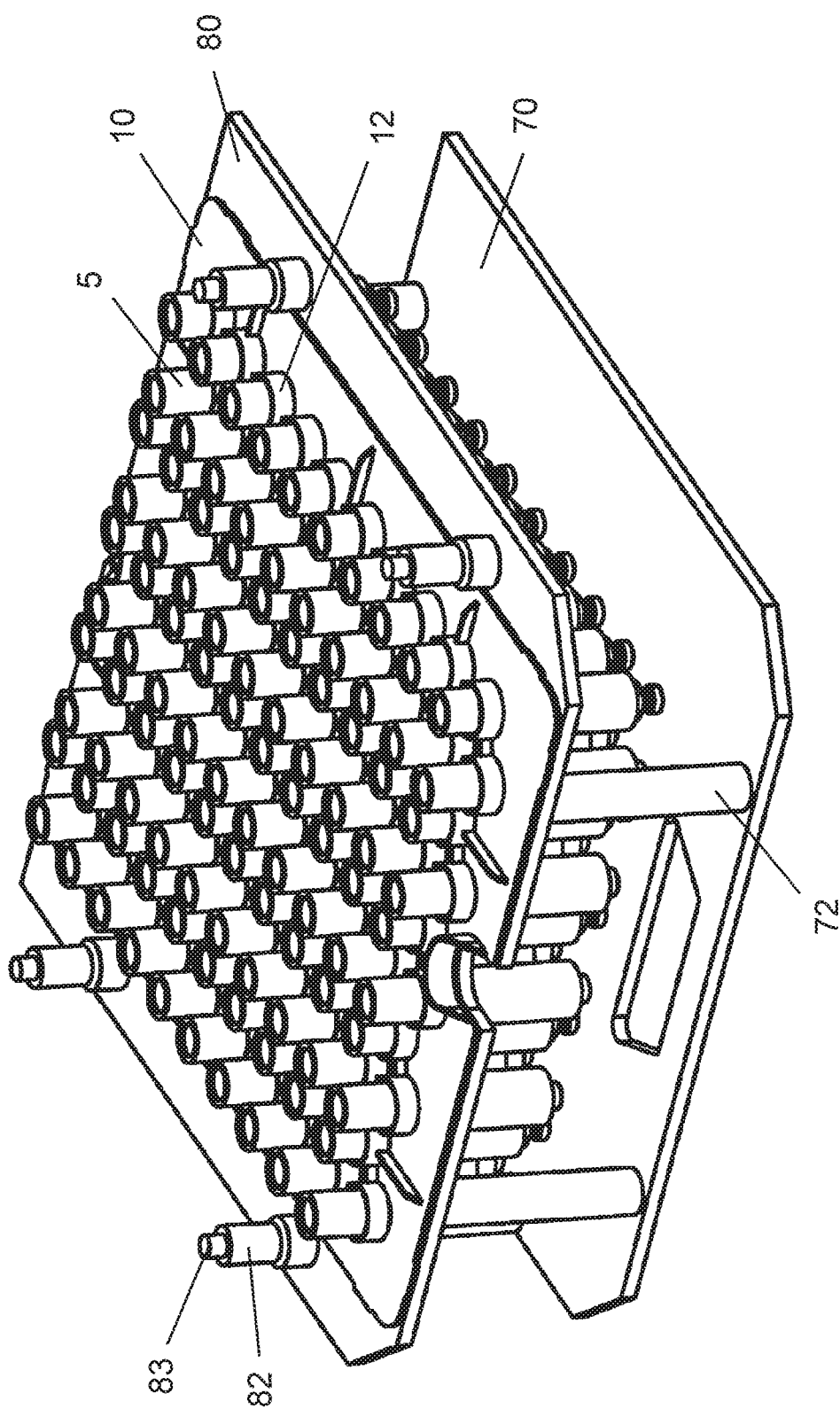
Figure 14C:
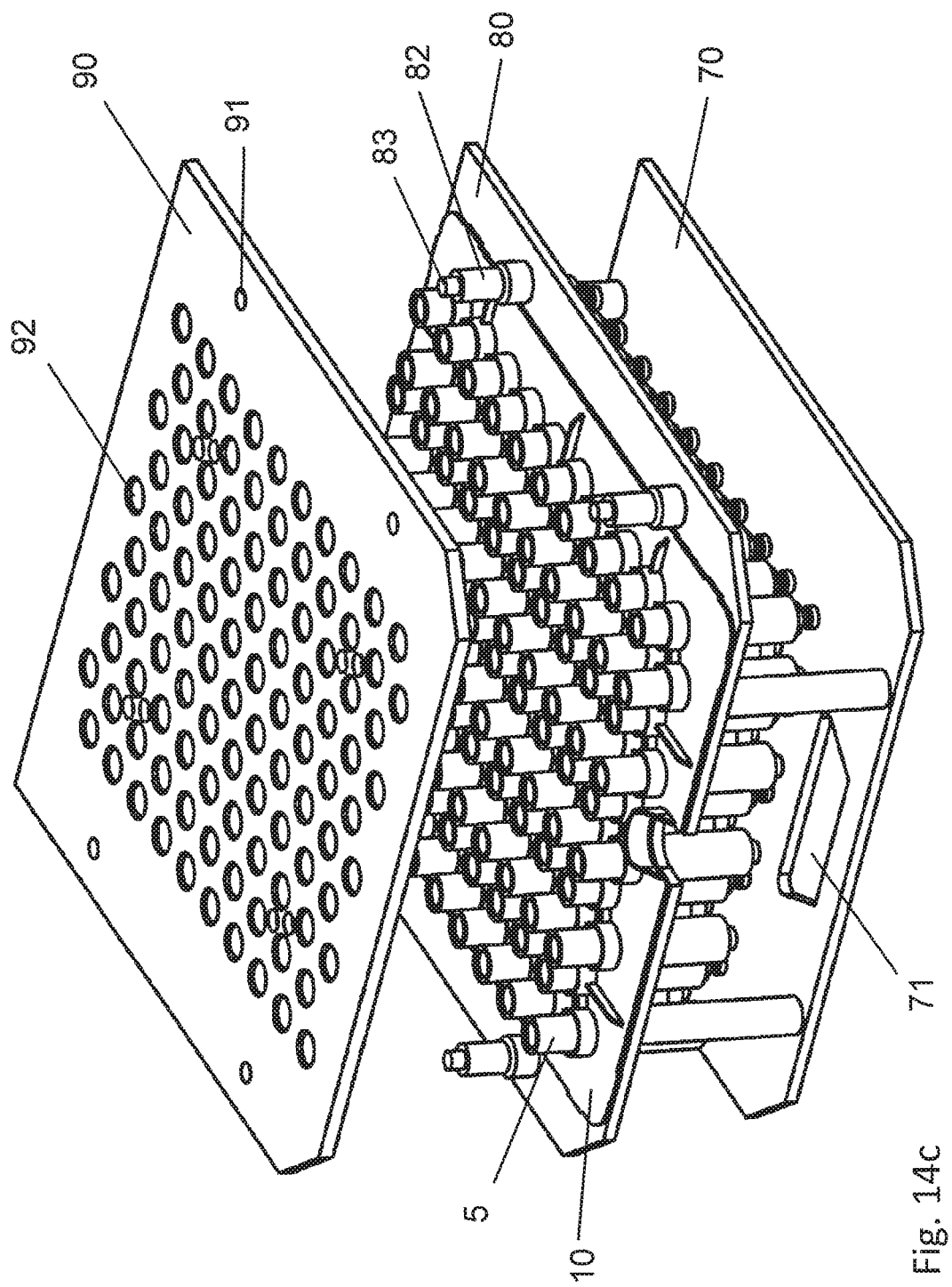
Figure 14D:
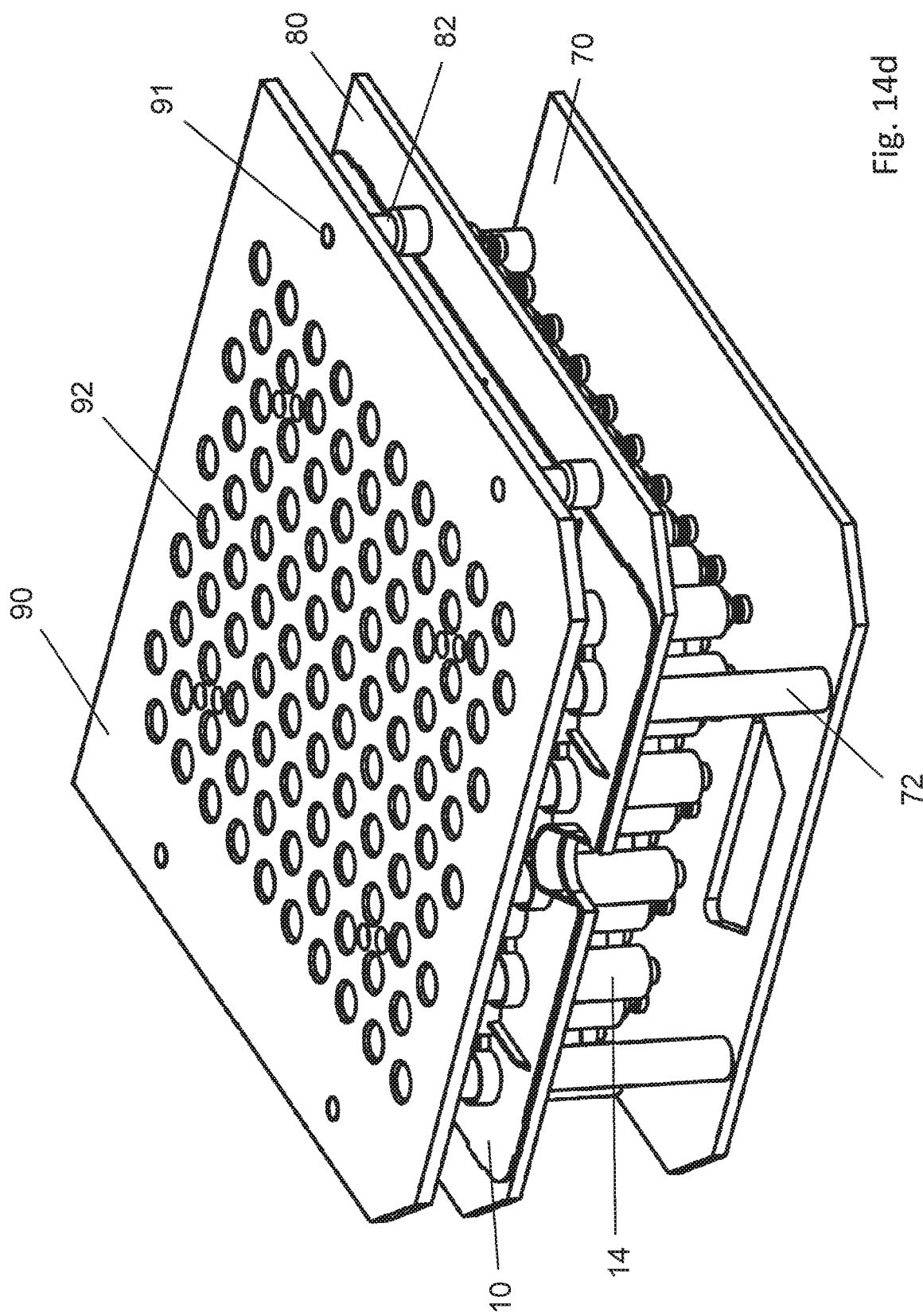
Figure 14E:
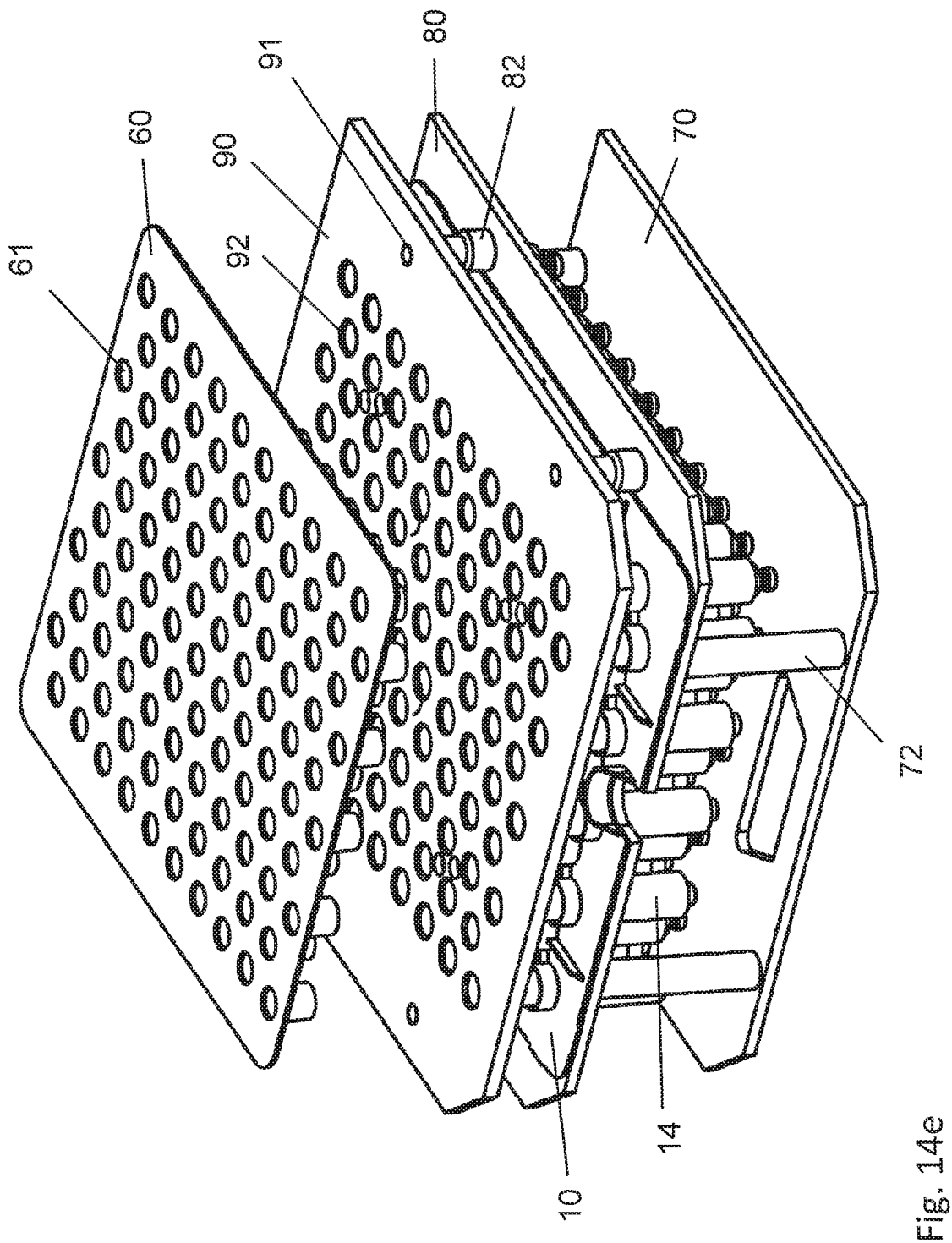
Figure 14F:
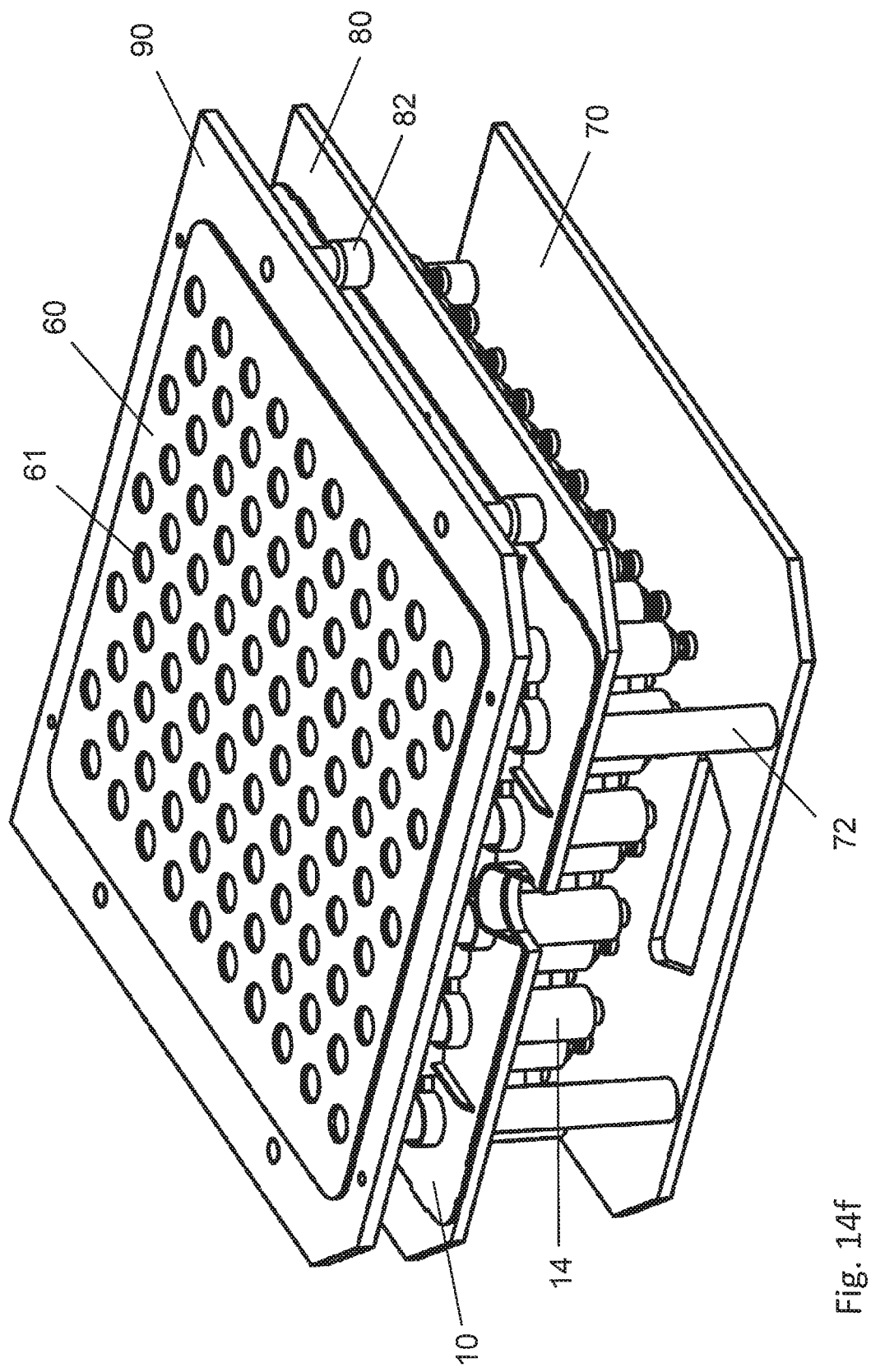
Figure 14G:
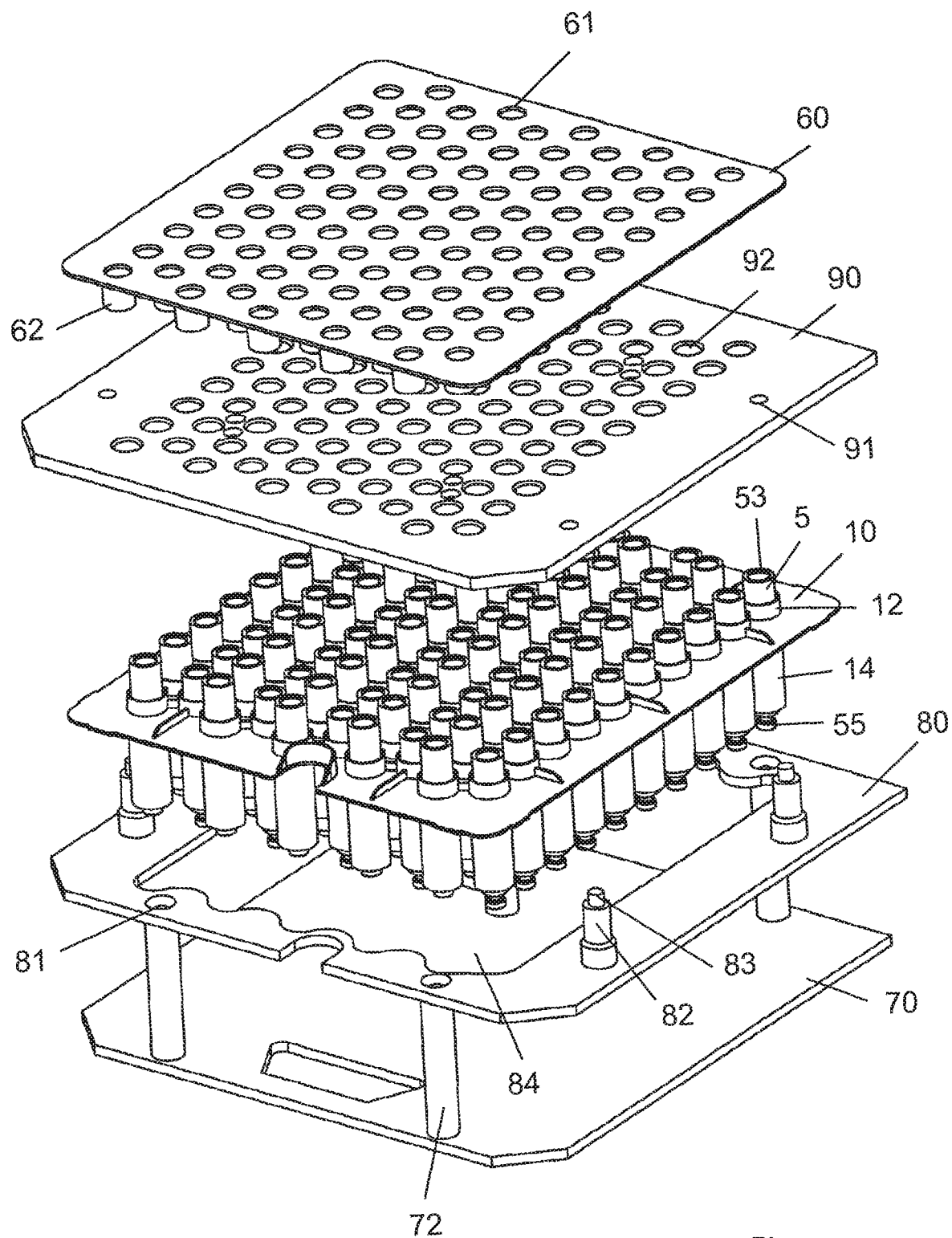

FIG. 6*a* is an enlarged partial view from FIG. 5 showing how the cartridges are supported inside the receptacles of the supporting structure according to the present invention;

FIG. 6*b* is a sectional view of a cartridge shown in FIG. 6*a*;

FIG. 7 is an exploded view showing a transport or packaging container together with the supporting structure of FIG. 1 (tub and nest assembly for cartridges) with cartridges inserted into the receptacles of the supporting structure and with one cartridge sealed at a bottom end thereof;

FIG. 8 is an enlarged partial view of the tub and nest assembly for cartridges of FIG. 7;

FIG. 9 shows the tub and nest assembly for cartridges of FIG. 7 with the supporting structure for cartridges inserted and a sealing lid sealed on an upper edge of the transport or packaging container;

FIG. 10 is a schematic top view of a processing station for processing sealed cartridges using the supporting structure for cartridges in a filling process;

FIG. 11 is a schematic cross-sectional view of the tub and nest assembly at a filling station used in a process according to the present invention;

FIGS. 12*a*-12*c* show details of a supporting structure for closures for cartridges according to a first embodiment of the present invention;

FIGS. 12*d*-12*e* show the accommodation of closures in the receptacles of a supporting structure for closures for cartridges according to a further embodiment of the present invention;

FIGS. 13*a*-13*d* show a transport or packaging container together with the supporting structure of FIG. 12*a* (tub and nest assembly for closures) for accommodating a plurality of closures for cartridges, at various stages of providing the transport or packaging container for closures;

FIGS. 14*a*-14*f* show a setup for simultaneously closing (stoppering) a plurality of cartridges using a nest for closures and a nest for cartridges with their receptacles in alignment at various stages;

FIG. 14*g* shows this setup in a perspective exploded view; and

Figure 15:
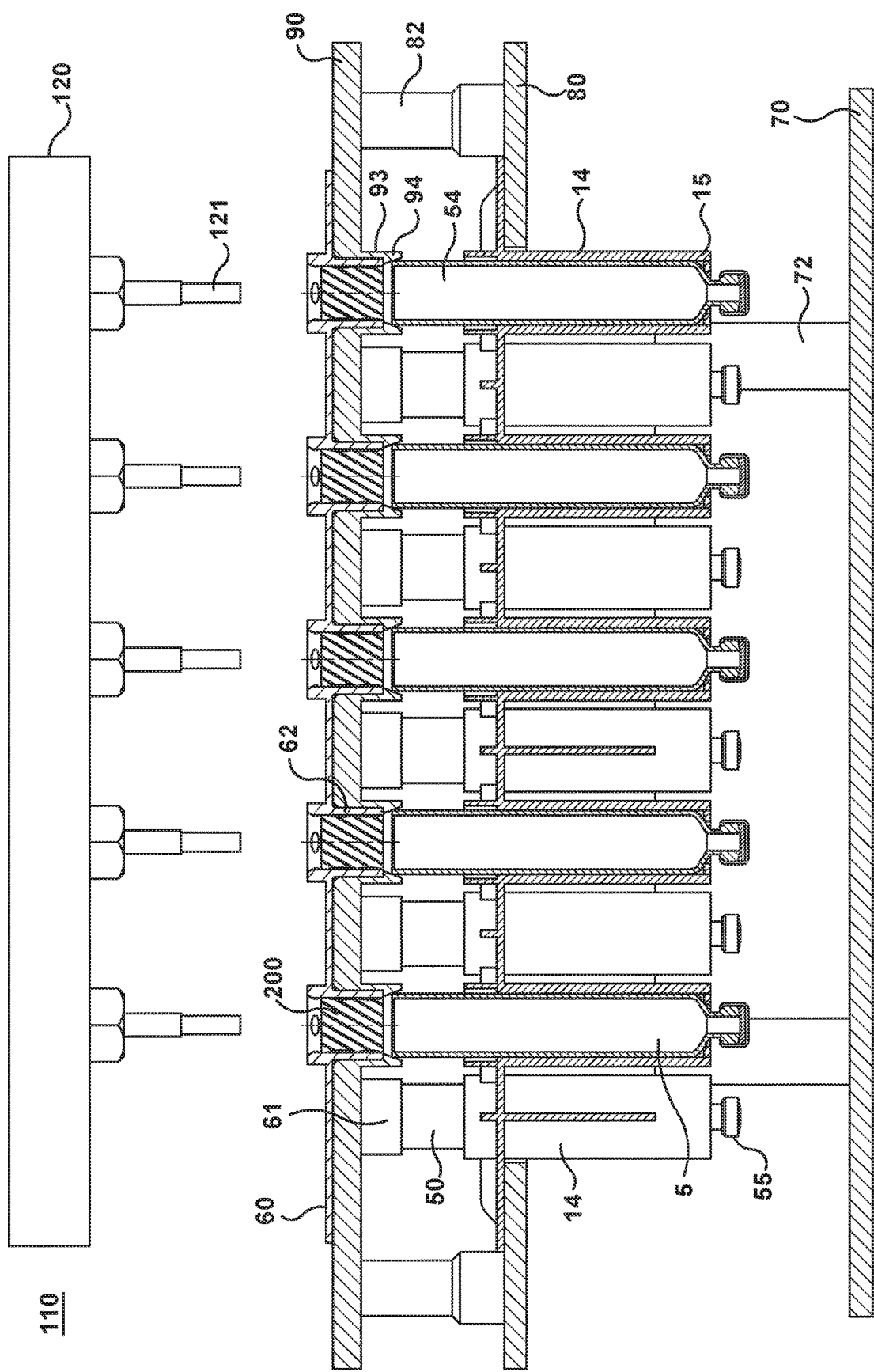

FIG. 15 shows a method according to the present invention for simultaneously closing (stoppering) a plurality of cartridges in a schematic sectional side view.

Throughout the drawings, the same reference numerals designate identical or substantially the same components or groups of components.

DETAILED DESCRIPTION OF PREFERRED EMBODIMENTS

A supporting structure (in the following nest for cartridges or cartridge nest) in the sense of the present invention and as disclosed in Indian patent application no. 1590/MUM/2015 and PCT-application no. PCTIN2015000394 of the Applicant is used for concurrently supporting a plurality of sealed cartridges for use in pharmaceutical, medical or cosmetic applications.

Such cartridges, including pen cartridges, by-pass cartridges and dental cartridges, are a commonly-used packaging solution for drug delivery systems, e.g. insulin administration, pen systems, pump systems, auto-injectors and needle free injectors. For special requirements such as by-pass and chemically strengthened cartridges, personalized designs are available on the market. Cartridges available on the market may be made of glass material, particularly of Fiolax® glass from SCHOTT AG, and offer fixed volumes for drug delivery of e.g. 1.0 ml, 1.5 ml and 3.0 ml. Different volumes usually correspond to different axial lengths of the cartridges.

An example for such a cartridge embodied as a syringe barrel is shown in FIG. 6*b* and comprises an upper end with a filling opening 53, a bottom end 52 opposite to the upper end and a cylindrical body 50 of a first outer diameter, which is usually identical with the diameter of the filling opening 53 at the upper end of the syringe barrel. The cylindrical body 50 merges into a tapered shoulder portion 51 at the bottom end of a reduced diameter, which is followed by a widened bottom rim 52 with a secondary opening 54 used for drug administering. After filling the cylindrical body 50, the filling opening 53 is closed by means of an elastomeric closure provided with or without a fluoropolymer barrier coating, such as a thick rubber or plastic plug, which later acts as a piston when the content is pressed out for drug administering. The secondary opening 54 is sealed by a seal, usually with a rubber plug with septum (puncture rubber) provided with or without a fluoropolymer barrier coating or with a combiseal. For protecting the septum and fixing the plug an outer closure (beaded cap or cramp), often made from an aluminum sheet or aluminum/plastic compound material, is used, which is usually crimped over the widened bottom rim 52 to thereby tightly secure the seal at the cartridge and thereby form a pre-crimped cartridge in the sense of the present application. In the cross-sectional view of FIG. 6*b* such a pre-crimped cartridge including a seal 55 of the type mentioned above is shown on the right-hand and left-hand side of the drawing, whereas the central cartridge is shown in a cross-section and without such a seal. As can be concluded from FIG. 6*b*, a predetermined axial length is defined between the upper end and the bottom end of the cartridge. Particularly, cartridges in the sense of the present invention do not have hand rests at their upper ends as conventional syringe bodies, and, if they would have such fingers rests, these hand rests would not be supported directly on a supporting plate or on members thereof, as outlined in more detail in the following, when such cartridges were accommodated in a nest.

Referring to FIGS. 1 to 4, a supporting structure for cartridges (in the following nest for cartridges or cartridge nest) comprises a planar supporting plate 10 having a plurality of tubular receptacles 11 disposed in a regular arrangement, which at least extend downward from the bottom side of the planar supporting plate 11 (see bottom view of FIG. 4), and preferably also protrude upward from the upper side of the supporting plate, as shown in the perspective top view of FIG. 1. Thus, the tubular receptacles 11 are formed by the circumferential side-walls 12, 14 protruding from the upper and bottom side of the supporting plate 10, respectively. Preferably these side-walls 12, 14 are of cylindrical shape for accommodating the cartridges, although other shapes, such as polygonal shapes are also possible. These receptacles 11 are disposed in a regular two-dimensional arrangement, at equidistant spacing. As shown in the top view of FIG. 2, virtual connecting lines between the centers of directly adjacent receptacles 11 respectively may form a hexagon with a further receptacle 11 disposed at a center of the respective hexagon. According to other embodiments, the receptacles may also be disposed at equidistant spacing along two mutually orthogonal directions.

The inner diameter of the receptacles is slightly larger than the outer diameter of the cartridges to be accommodated. For enabling a precise centering of the cartridges, a plurality of ribs 13 is formed on the inner circumferential surfaces of the side-walls 12, 14 protruding radially inward. These ribs 13 are formed at equidistant angular spacing on the inner surfaces of the side-walls 12, 14, preferably at diametrically opposite positions thereof, so that the total number of these ribs 13 may be e.g. equal to four or eight.

The upper ends of these ribs 13 preferably do not extend up to the upper rim of the side-walls 12. In order to enable a smooth insertion of the cartridges into the receptacles 11, the upper ends of the ribs 13 are preferably slanted radially inward to guide the cartridges upon insertion. Together, the ribs 13 span an inner volume of a diameter, which essentially equals the outer diameter of the cartridges, thus enabling an essentially rattle-free storage of the cartridges and a smooth, rattle-free axial movement of the cartridges upon insertion into or removal out of the receptacles 11. The ribs 13 enable a precise centering of the cartridges at predetermined positions, so that automated processing systems may expect the cartridges at precisely predetermined positions upon their transfer to a processing station, which significantly reduces the efforts required for automation.

As shown in FIG. 6a, the axial length of the receptacles 11 is smaller than the axial length of the cartridges to be accommodated, so that in use the upper ends with the filling openings 53 extend beyond the upper rim of the upper side-walls 12 of the receptacles so that the filling openings 53 are freely accessible for processing, e.g. for performing a filling operation as shown in FIG. 11.

Figure 4:
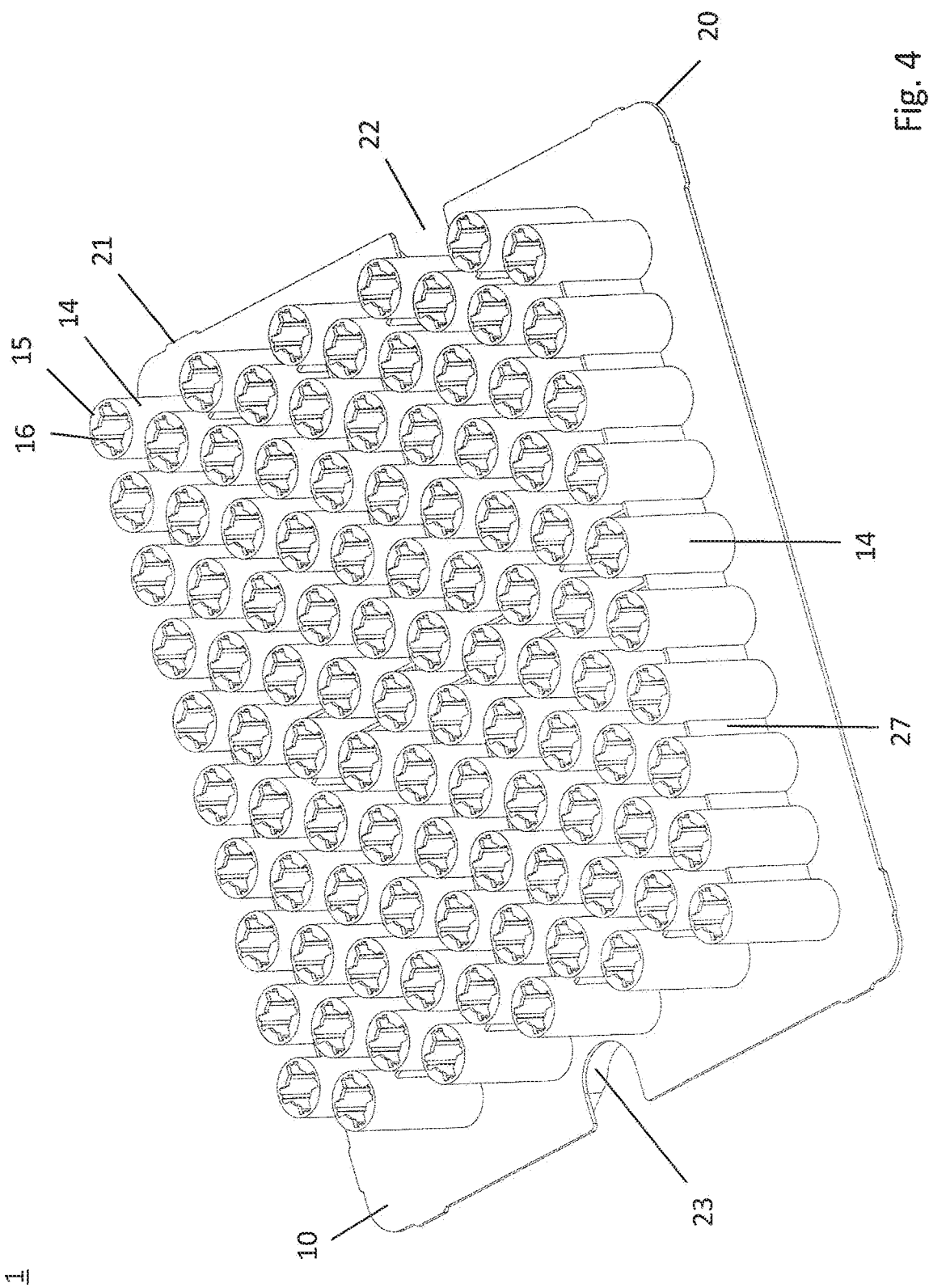
FIG. 4 is a perspective bottom view of the supporting structure of FIG. 1.

As shown in FIGS. 4 to 6, retaining protrusions 15 are formed at the bottom ends of the receptacles 11 protruding radially inward. These retaining protrusions 15 are mated with the shoulder portions 51 of the cartridges in such a manner that the shoulder portions 51 are directly supported on the retaining protrusions 15 of the receptacles 11 when the cartridges are accommodated upside-down in the receptacles 11, as shown in FIG. 6. Furthermore, the axial length of the receptacles is mated such to that of the cartridges that the upper ends of the cartridges protrude from the upper ends of the receptacles 11, as shown in FIG. 6.

Figure 3:
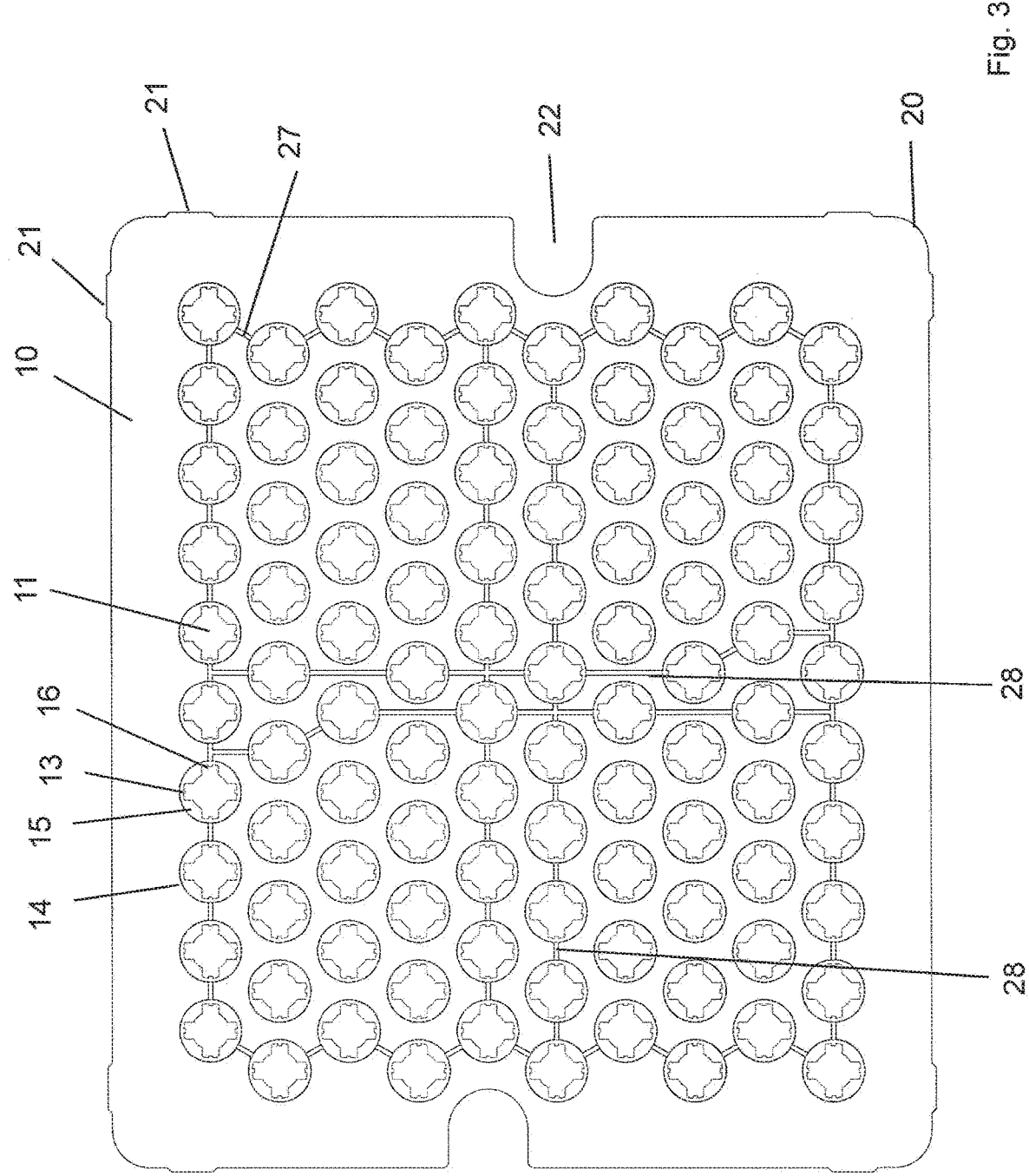
FIG. 3 is a bottom view of the supporting structure of FIG. 1.

As shown in FIGS. 3 and 4, the retaining protrusions 15 are formed as ring segments that protrude radially inward at the bottom ends of the receptacles 11 and at equidistant angular spacing, preferably at diametrically opposite positions. As shown in FIG. 3, gaps 16 of essentially rectangular profile are formed between adjacent ones of the retaining protrusions 15. These gaps 16 preferably extend up to the inner surface of the side-walls 14 of the receptacles 11. The afore-mentioned axial ribs 13 may extend downward to the retaining protrusions 15, but for a precise centering of the cartridges this is not essential.

For a smooth and more stable and precise supporting of the cartridges, the front ends of the retaining protrusions 15 may be slanted or wedge-shaped in correspondence with the outer contour of the shoulder portions 51 of the cartridges to be accommodated.

As shown in FIG. 6b, the outer diameter of the sealed or pre-crimped cartridges 5 at their sealed bottom ends is larger than the outer diameter at their shoulder portions 51 but smaller than the (first) outer diameter of the cylindrical body 50. Further, the thickness of the retaining protrusions 15 in axial direction is smaller than the axial length of the sealed bottom ends of the sealed cartridges 5 so that the sealed bottom ends of the sealed cartridges extend through central openings 17 (shown in FIG. 5) formed by the retaining protrusions 15 at the bottom ends of the receptacles 11.

The supporting plate 10 of a nest 1 according to the present invention is preferably formed of a plastic material and the side-walls 12, 14 of the receptacles 11 and the retaining protrusions 15 are thus formed unitary with the supporting plate 10. For enabling a stoppering of the filling openings 53 with rubber plugs or syringe plungers while the cartridges are accommodated in the receptacles 11 of the nest 1, the retaining protrusions 15 are preferably configured to sustain typical axial forces exerted onto the sealed cartridges upon stoppering of up to 500 N, preferably of up to 750 N and more preferably of up to 1,000 N, which can be ensured easily by a suitable choice of the plastic material and material strength of the supporting plate 10 and all its members.

Figure 2:
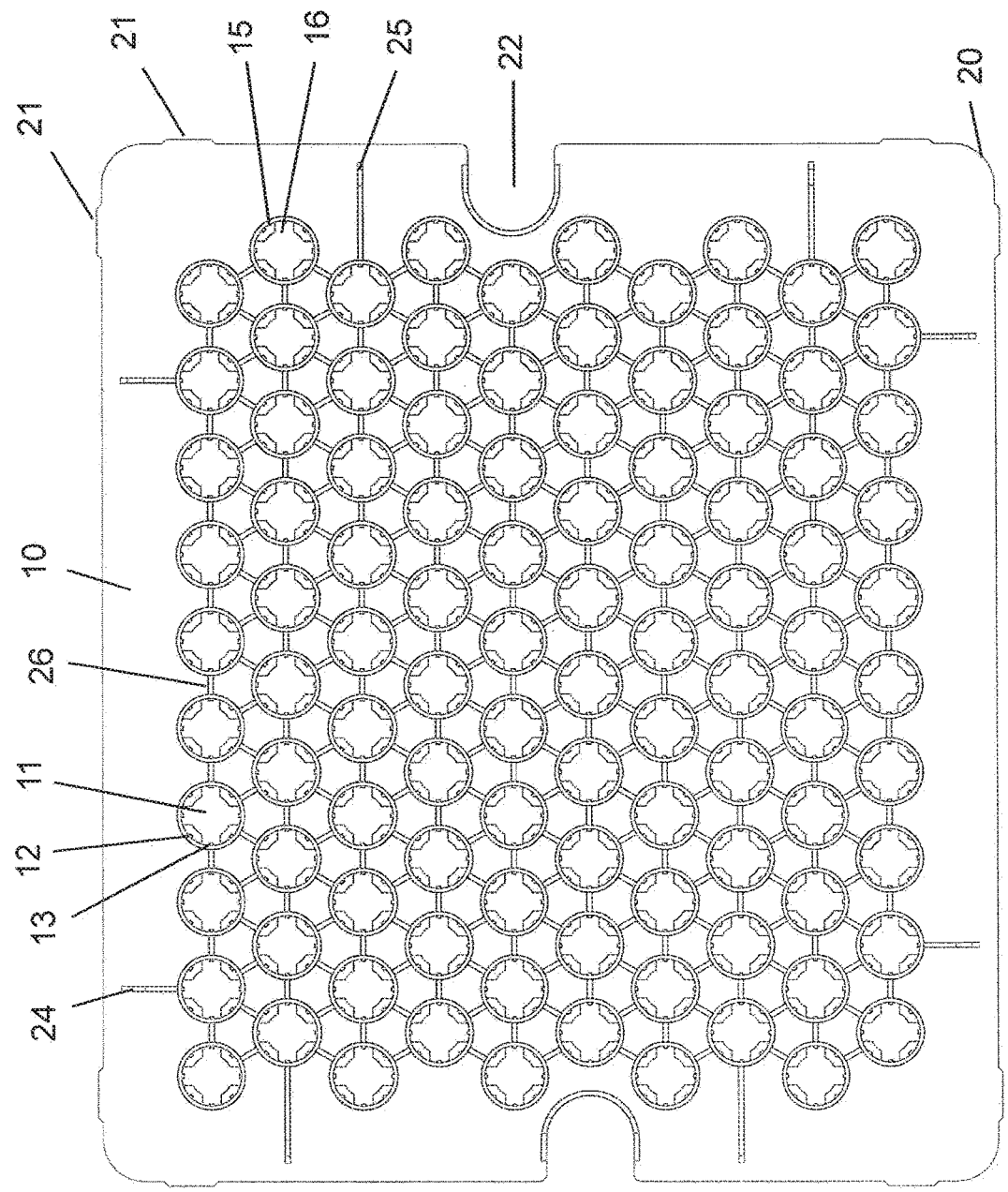
FIG. 2 is a top view of the supporting structure of FIG. 1.

As shown in FIGS. 2 and 4, for stiffening the supporting plate 10, stiffening ribs 26, 28 may be provided on the upper side and bottom side, respectively, of the supporting plate 10, connecting the upper side-walls 12 and bottom side-walls 14 of the receptacles. In the arrangement of the receptacles 11 shown in FIG. 2, these stiffening ribs 26 thus form hexagons interconnecting directly adjacent ones of the receptacles and triangles connecting the outer ones of these receptacles with a further receptacle 11 disposed in the center of a respective hexagon. As shown in FIG. 4, these stiffening ribs 28 may interconnect the side-walls 14 of the outer ones of the receptacles 11. Furthermore, central stiffening 28 may also be provided near the center of the supporting plate 10, for interconnecting central ones of these receptacles 11. In a preferred embodiment, such a nest 1 will be made of a plastic material using plastic injection-molding techniques. Despite the afore-mentioned stiffening measures, the supporting plate 10 may still be flexible to a certain extent, if required.

For the transport, storage and packaging of a nest 1 as outlined above together with the cartridges accommodated therein a transport or packaging container 3 (hereinafter also named tub for cartridges) is used as schematically shown in FIG. 7. According to FIG. 7, the transport or packaging container 3 is essentially box-shaped or tub-shaped and has a base 30, a circumferential side wall 31 protruding essentially in vertical direction therefrom, a supporting step 32 protruding essentially rectangular therefrom, a circumferential upper side wall 33 and an upper rim 34 which is formed as a flange. The corners 35 of the transport or packaging container 3 are suitably formed rounded, particularly near the supporting step 32. Preferably, the upper side wall 33 is formed inclined at a small angle of inclination with respect to a vertical to the base 30 in order to ease the insertion of the nest 1. Such a transport or packaging container 3 is preferably formed from a plastics material, particularly by plastic injection molding, and is preferably formed of a clear transparent plastic in order to enable a visual inspection of the nest 1 accommodated in the transport or packaging container 3 and of the cartridges 5 supported by it.

In this manner, the nest 1 can be positioned precisely in the transport or packaging container 3 and thus the plurality of cartridges 5 can be positioned and held in a regular array and at precisely defined positions in a transport or packaging container 3 with standardized dimensions. In particular, it can be ensured in this way that all bottoms or bottom ends of the cartridges are positioned in a plane defined jointly and in parallel to the base 30 and that all upper ends are positioned in a plane defined jointly and parallel to the upper rim 34 of the transport or packaging container 3. As shown in FIG. 9, the upper ends of the cartridges do not extend beyond the upper rim 34 of the transport or packaging container 3 but are spaced apart to the upper rim 34.

As shown in FIG. 9 a packaging unit (also named tub and nest assembly) formed by the transport or packaging container (tub) 3 and the nest 1 with the cartridges 5 accommodated therein is closed or sealed at least on the upper side by means of a protective foil or packaging foil 6 bonded onto the upper flange-like edge 34 of the tub 3. Thus, it is ensured that the interior of tub 3 is hermetically sealed from the environment, from manufacture until the time when access is to be gained to the interior of the tub 3 for further processing of the cartridges 5. The protective foil 6 may be in particular a gas-permeable plastic film, in particular a web of synthetic fibers such as polypropylene fibers (PP) or a Tyvek® protective film, which enables a sterilization of the cartridges accommodated therein through the film 6.

As will become apparent to a person skilled in the art, the bottom side of the transport or packaging container (tub) 3 may also be formed open, e.g. in the manner of the tub 3 shown in FIG. 9, i.e. in the manner that also the bottom side of the tub is provided with a flange-like bottom rim in the manner of the upper rim 34 so that the bottoms of the cartridges 5 may be freely accessible for processing steps also from the underside of the tub 3 if required.

As shown in FIGS. 1 and 2, for enabling an easy insertion of nest 1 into tub 3 and removal from the latter, access apertures 22 are formed on two longitudinal sides of the supporting plate 10, via which gripping arms or the like may grab nest 22. As shown in FIG. 1, the access apertures 22 are partially surrounded by upright side-walls 23 to prevent a collision of the gripping arms or the like with the cartridges accommodated. As shown in FIG. 1, the access apertures 22 are displaced relative to each other, e.g. by one row, which further facilitates an unambiguous positioning of nest 1 in tub 3.

A packaging unit as shown in FIG. 9 accommodating presterilized prefillable cartridges or syringe barrels can be stored under save and sterile conditions and then supplied to pharmaceutical customers for further processing. Particularly, the pharmaceutical customers will then fill medicine or other liquids into the presterilized nested syringe barrels via the filling openings using conventional filling and stoppering machines, which may be any of the three following types of filling and stoppering machines: 1) manual machines, 2) semi automatic machines and 3) fully automatic machines.

An example of such a filling operation is shown in FIG. 11 in a schematic cross-sectional view. At the time of delivery under sterile conditions, the packaging unit will be sealed by a lid or protective foil as outlined above (not shown), while the nest 1 will be supported on the supporting step 32 of tub 3. At the time of delivery under sterile conditions, the packaging unit may be packages further in at least one sterile plastic bag. The cartridges 5, which are sealed by seals 55, e.g. pre-crimped, at their bottom ends will be accommodated upside-down in the receptacles of nest 1 so that their filling openings 53 face toward the upper end of tub 3 and the lid or protective foil (not shown). The height level of the upper ends of cartridges 5 is thus precisely defined in relation to the level of the supporting plate 10, which is essentially equal to the level of supporting step 32 of tub 3, because the supporting plate 10 rests directly on supporting step 32.

The exemplary filling process shown in FIG. 11 considers that the supporting plate 10 rests directly on a rectangular holding frame 40 after removal from tub 3. The inner free width of the holding frame 40, however, also allows for a direct support of the outer side of supporting step 32 on the holding frame. In either case the height level of the upper ends of cartridges 5 is precisely defined in relation to the level of the holding frame 40.

For performing the filling process, the holding frame 40 is transferred at a precisely defined height level to a filling station comprising a row of filling nozzles 41 supported by a holding arm 42 used for injecting a liquid, e.g. a medicine, via the filling openings 53 into the cartridges 5 supported by nest 1. Also the height level of the bottom ends of filling nozzles 41 is precisely defined so that a non-zero gap of well-defined width $\Delta z$ will be ensured between the upper ends of the cartridges 5 and the bottom ends of filling nozzles 41. Usually, the width $\Delta z$ of this gap will be precisely adjusted before performing the process and will be part of the general settings of a processing station. The width $\Delta z$ of this gap will be adjusted in accordance with general safety regulations, in particular in accordance with GMP (Good Manufacturing Practice) guidelines requirements.

For a given length of the cartridges 5 to be supported in a nest 1, the height level of the upper ends of the cartridges 5 will be precisely defined by the axial lengths of the receptacles 11 of nest 1 and thus by the height level of the retaining protrusions 15. Thus, if different types of cartridges 5 with different axial lengths are to be processed by one and the same processing station, according to the present invention no change of the general settings of the processing station is required. Rather, only a different type of nest 1 with receptacles 11 of different axial length needs to be used to thereby ensure that also the different type of cartridge 5 will be fed to the processing station at the same height level of the upper ends of the different type cartridges 5.

As the different type of nest 1 required for the different type of cartridge 5 together with the sealed cartridges 5 accommodated therein can be inserted into the packaging unit in the same manner and as the whole packaging unit can be sealed and transported under sterile conditions to the pharmaceutical customers, according to the present invention it can be ensured that also the different type of cartridge may be processed under the same settings and conditions without the need of adjusting the general settings of the processing station. Furthermore, no additional hygienic permissions will be required for this purpose. Thus, according to the present invention different types of cartridges involving different axial lengths may be processed in the same way and under the same general conditions and settings. Thus, the present invention enables a cost-efficient processing of presterilized, sealed cartridges.

As will become apparent to the person skilled in the art, the above principle of replacement of one type of nest by a different type for compensating for different axial lengths of batches of different types of cartridges also works for compensating for different outer diameters of batches of different types of cartridges. More specifically, if a first batch of cartridges having a first outer diameter and a second batch of cartridges having a second outer diameter different to the first outer diameter needs to be processed by the same processing station, according to the invention only a first type of nest used for the first batch of cartridges and having receptacles of a diameter corresponding to the first outer diameter needs to be replaced by a second type of nest to be used for the second batch of cartridges and having receptacles of a diameter corresponding to the second outer diameter.

As will become apparent to the person skilled in the art upon studying of the above, the afore-mentioned principle may also be applied if access to the bottom ends of the cartridges is required, because also the height level of the bottom ends of all cartridges accommodated by a nest is precisely defined in relation to the height level of the holding frame 40. This even applies if the tub 3 should be supplied to the pharmaceutical customer with an open bottom sealed by a lid or protective foil.

FIG. 12a shows a supporting structure for closures (in the following nest for closures or closure nest) in a perspective bottom view, which comprises a planar supporting plate 60 having a plurality of tubular receptacles 61 disposed in a regular arrangement, which at least extend downward from the bottom side of the planar supporting plate 60, and preferably also protrude upward from the upper side of the supporting plate 60, as shown in the sectional views of FIGS. 12d and 12e for a further embodiment. Thus, the tubular receptacles 61 are formed by the circumferential side-walls 62, 63 protruding from the upper and bottom side of the supporting plate 60, respectively. Preferably these side-walls 62, 63 are of cylindrical shape for accommodating the closures 200, although other shapes, such as elliptic shapes might also be possible. These receptacles 61 are disposed in the same regular two-dimensional arrangement as for the supporting structure for cartridges set forth above, at equidistant spacing.

FIG. 12c shows the insertion of a plurality of closures 200, such as elastic plugs or plunger stoppers, into the receptacles 61 of the closure nest 2. For this purpose, the closures 200 are inserted from above or below into the receptacles 61 to a desired extent, preferably until they are fully accommodated in the receptacles and the upper ends of the closures are at a minor distance to the upper ends of the upper side-walls 63 as defined by the retaining structures inside the receptacles 61, as shown in FIG. 12e.

For retaining the closures 200 reliably in the receptacles 61, particularly for avoiding that the closures 200 simply slide out of the receptacles 61 during handling of the closure nest which might include reversing the orientation of the closure nest, the receptacles 61 comprise retaining structures 66, 67 for releasably engaging with the closures 200 for retaining the closures in the receptacles. More specifically, the retaining structures 66, 67 are formed on inner sides of the circumferential side walls 62, 63 of the receptacles 61 and configured to cooperate with the closures in a form-fitting manner.

As shown in FIG. 12e, the retaining structures comprise protrusions 66, 67 formed on the inner sides of the circumferential side walls 62, 63 of the receptacles. The protrusions 66, 67 may be formed as circumferential protrusions on the inner sides of the circumferential side walls 62, 63 of the receptacles 61. Preferably, the protrusions 66, 67 are formed at equal angular distances along the inner sides of the circumferential side walls 62, 63 of the receptacles 61.

At least one of the protrusions may be configured to mate to the outer contour of the closures 200 to be accommodated. As shown in FIG. 12e, the closures 200 may have an undulated outer contour, having several circumferential concave recesses 202 or bulges 201, and the protrusions may be formed to at least partially mate this outer contour.

As shown in FIG. 12e, the receptacles 61 comprise upper retaining structures 66 formed at an upper end of the receptacles 61 and bottom retaining structures 67 formed at a bottom end of the receptacles 61, wherein the distance between the respective upper and bottom retaining structures is basically equal to the axial length of the closures 200 so that the closures 200 may be retained loosely, i.e. even with radial and/or axial play, between the two retaining structures 66, 67, or at least with minor friction only.

As shown in FIG. 12e, the upper retaining structures 66 are formed as convexly curved protrusions protruding from the inner sides of the upper circumferential side walls 63 of the receptacles 61, whereas the bottom retaining structures 67 are formed as hook-like protrusions protruding from the inner sides of the lower circumferential side walls 62 of the receptacles 61.

According to FIG. 12e, the bottom retaining structures 67 may be beveled on an upper side thereof to support the bottom side of the closures 200 thereon and reduce the forces required for pushing of the closures 200 downward. According to FIG. 12e, the bottom retaining structures 67 may also be beveled on a lower side thereof so that the receptacles may rest directly and without inducing tension on the upper ends of cartridges during stoppering, as shown in FIG. 15 and outlined below in more detail.

Figure 13A:
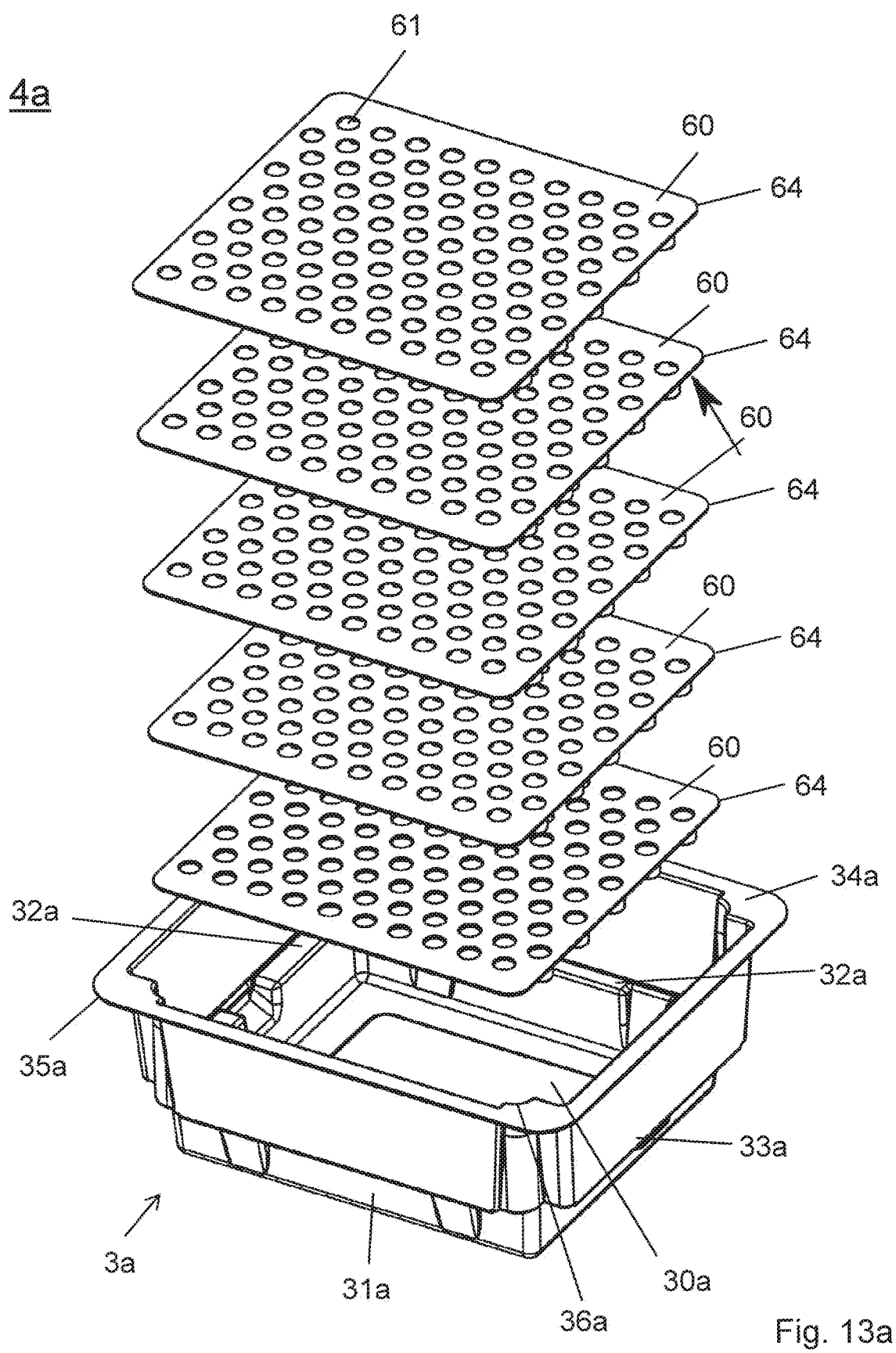

For the transport, storage and packaging of a nest 2 as outlined above together with the closures accommodated therein a transport or packaging container 3a (hereinafter also named tub for closures) is used as schematically shown in FIG. 13a. According to FIG. 13a, the transport or packaging container 3a has basically the same configuration as described above with reference to FIG. 7 and is essentially box-shaped or tub-shaped and has a base 30a, a circumferential side wall 31a protruding essentially in vertical direction therefrom, a supporting step 32a protruding essentially rectangular therefrom, a circumferential upper side wall 33a and an upper rim 34a which is formed as a flange. The corners 35a of the transport or packaging container 3a are suitably formed rounded, particularly near the supporting step 32a. Preferably, the upper side wall 33a is formed inclined at a small angle of inclination with respect to a vertical to the base 30a in order to ease the insertion of the nest 2. Such a transport or packaging container 3a is preferably formed from a plastics material, particularly by plastic injection molding, and is preferably formed of a clear transparent plastic in order to enable a visual inspection of the nest 2 accommodated in the transport or packaging container 3a and of the closures accommodated in it. The rounded corners 64 of the supporting plate 60 mate to the inner rounded corners 36a of the tub 3a, at least if disposed at the bottom end of the upper side walls 33a.

As shown in FIG. 13a a plurality of nests 2 for closures can be accommodated inside the same transport or packaging container 3a stacked one above the other. In the stacked configuration, the lower ends of the side-walls of an upper of two adjacent supporting plates 60 may rest directly on the upper surface of the lower of two adjacent supporting plates 60. Because the outer diameter of the receptacles 61 (see FIG. 12e) is larger than the inner diameter of the receptacles 61, the side-walls 64 will not penetrate into the upper ends 65 of the receptacles 61. Thus, no spacers are required between adjacent supporting plates, which contributes to optimizing the packing density.

Figure 13B:
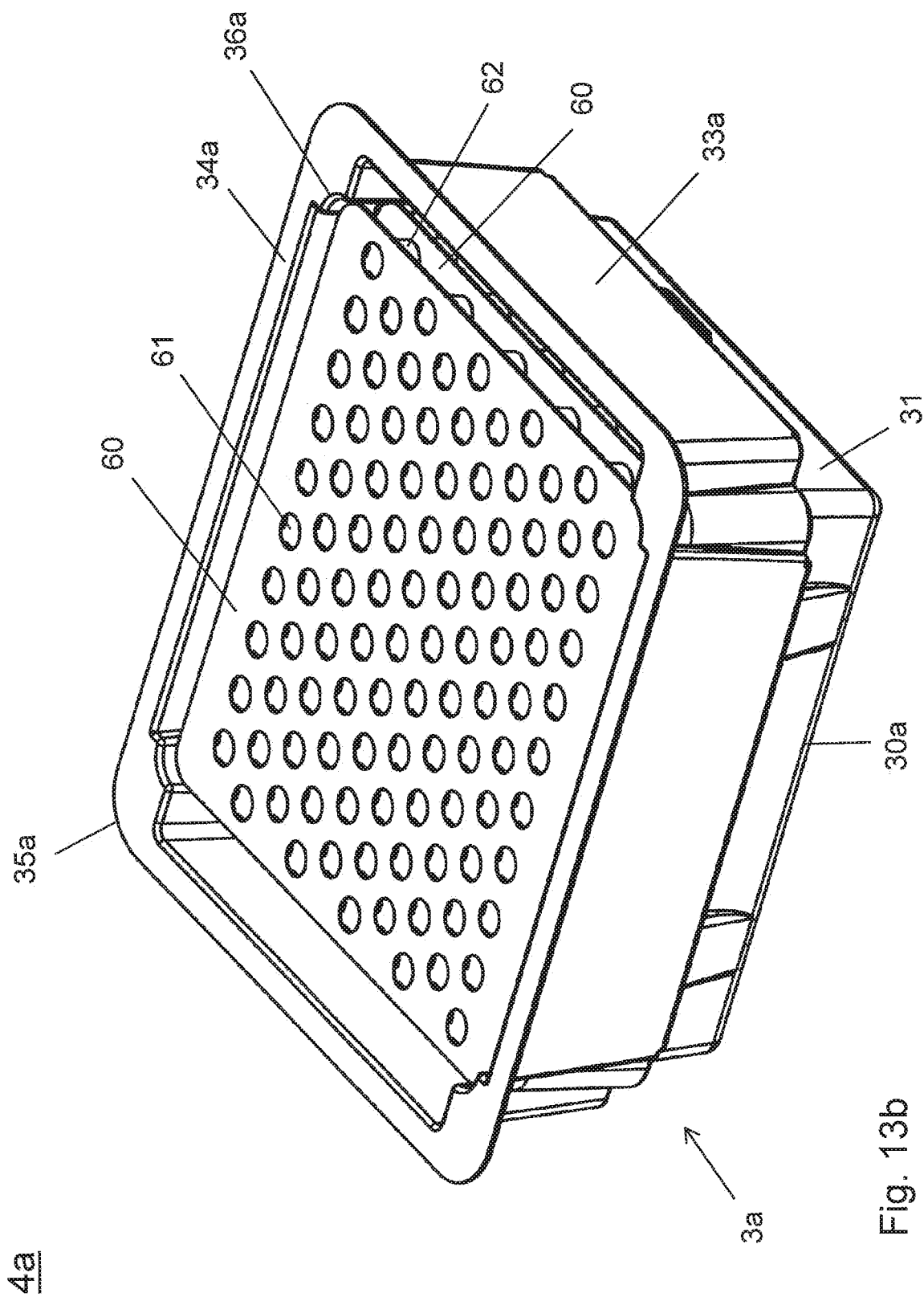

FIG. 13b shows the tub and nest assembly 4a with all nests inserted into the tub 31a for closures. For reasons of clarity, the closures are omitted in FIGS. 13a and 13b.

Figure 13C:
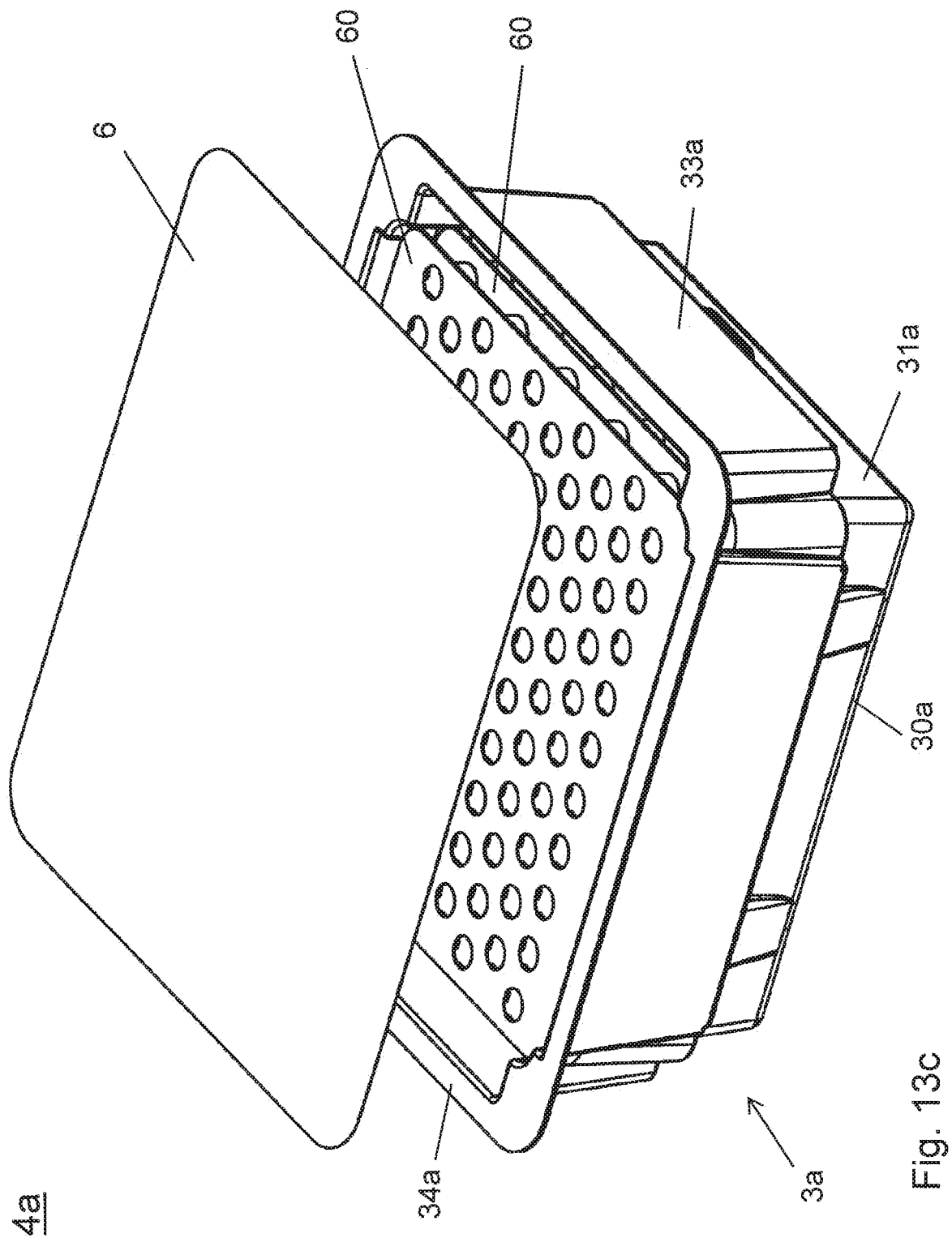

FIG. 13c shows a further stage of sealing the tub and nest assembly 4a of FIG. 13b, by sealing the upper end of tub 3a with a protective foil 6, which may be bonded to the circumferential flange 34a and may be gas-impermeable. Preferably, however, the protective foil 6 is a gas-permeable plastic film, in particular a web of synthetic fibers such as polypropylene fibers (PP) or a Tyvek® protective film, which enables a sterilization of the interior of the transport or packaging container 4a by a flow of a sterilizing gas through the protective foil 6.

FIG. 13d shows the tub and nest assembly 4a of FIG. 13c sterile sealed against the environment. In this condition the closures may be stored and transported under sterile conditions. For this purpose, the tub and nest assembly 4a may be packaged additionally in at least one gas-impermeable plastic bag.

Referring to FIGS. 14a to 14g, a general setup for closing (stoppering) cartridges according to the present invention will be described.

For supporting and aligning a supporting plate 10 of a cartridge nest in a predetermined position and orientation, a bottom holding frame 80 is used, which comprises a central opening 84, whose contour corresponds exactly to the outer counter of the cartridge nest.

More specifically, as shown in FIG. 1 the receptacles 11 of the cartridge nest 1 are aligned in rows along a first direction, but are not aligned in rows in a second direction perpendicular to this first direction. Instead, in the second direction each second receptacle 11 is offset e.g. by half a distance between two adjacent receptacles 11 in the first direction. The side-walls 12 of the receptacles 11 thus define an undulated contour along the second direction, i.e. in FIG. 1 along the left-hand and right-hand edge of supporting plate 10. Two opposite edges of the central opening 84 of the bottom holding frame 80 exactly correspond to this undulating pattern, so that the cartridge nest 1 can only be inserted in a given orientation that is unambiguously defined by the undulating pattern formed by the receptacles 11 of the cartridge nest 1. By means of the bottom holding frame 80 the upper ends of the cartridges 5 are positioned at a precisely defined height level relative to the machine holding frame 70, which may be part of a processing machine for the processing of containers and may be provided in a cleanroom or under sterile conditions, e.g. at a pharmaceutical company or filler.

As shown in FIG. 14a, several spacer rods 72 are disposed on the machine holding frame 70 for precisely defining the position and orientation of the bottom holding frame 80. For this purpose, alignment tips may be provided at the front ends of the spacer rods 72 that engage with the alignment holes 81 formed in the bottom holding frame 80.

FIG. 14b shows how the cartridge nest is accommodated and positioned in the opening of the bottom holding frame 80.

As shown in FIGS. 14a and 14c, several spacer rods 82 are disposed on the upper side of bottom holding frame 80 for precisely defining the position and orientation of an upper holding frame 90 used for positioning and aligning a closure nest above and relative to the underneath cartridge nest. Alignment tips 83 are provided at the front ends of the spacer rods 82 that engage with the alignment holes 91 formed in the upper holding frame 90.

FIG. 14d shows how the upper holding frame 90 is positioned and aligned on the bottom holding frame 80. A plurality of openings or receptacles 92 formed as through holes are formed in the upper holding frame 90 in exactly the same geometric arrangement as the receptacles of the underneath cartridge nest.

FIG. 14e shows how the supporting plate 60 of a closure nest is put onto the upper holding frame 90. For reasons of clarity the closures are omitted in FIGS. 14a-14g. As shown in FIG. 14e the supporting plate 60 of the closure nest is put onto the upper holding frame 90 in such a manner that the side-walls of the receptacles on the bottom side of the supporting plate 60 enter the openings or receptacles 92 of the upper holding frame 90 and are finally fully accommodated therein. Again, this can only be accomplished in a unique orientation and positioning that is unambiguously defined by the pattern formed by the openings or receptacles 92 of the upper holding frame 90.

Thus, in the condition of FIG. 14f all receptacles 61 of the supporting plate 60 of the closure nest are precisely aligned with all receptacles formed by the side-walls 14 of the cartridge nest and thus with all cartridges supported by the cartridge nest. FIG. 14g shows this exemplary set-up in a perspective exploded view.

FIG. 15 shows the set-up of FIG. 14f in a schematic sectional view. This set-up may be accomplished in a stoppering machine or in a combined filling and stoppering machine, in which case the bottom holding frame 80 could be identical with the holding frame 40 shown in FIG. 11 and the whole set-up will be disposed under reduced pressure or vacuum conditions at least while performing the stoppering process.

As shown in FIG. 15, the bottom ends of the side-walls 62 of the receptacles of the closure nest are precisely retained at the same level by hook-like protrusions 94 formed at the lower ends of the cylindrical side-walls 93 of the receptacles of the upper holding frame 90. More specifically, the lower ends of the side-walls 62 of the receptacles of the closure nest rest on the upper sides of the hook-like protrusions 94. As the upper holding frame 90, which is preferably made of a stable metal sheet, has a high mechanical stability and stiffness and will not flex during the stoppering process, the above alignment of the closures 200 with the underneath cartridges 5 will be maintained during all stages of the stoppering process.

As shown in FIG. 15, the lower ends of the cylindrical side-walls 93 of the receptacles of the upper holding frame 90 are beveled inwards so that they can snuggle to the open upper ends of the cartridges 5, if required. These lower ends may be coated with a resin or plastic to reduce tension in this region. During the stoppering process, preferably a very narrow gap exists between the upper ends of the cartridges 5 and the lower ends of the cylindrical side-walls 93 of the receptacles of the upper holding frame 90.

As shown in FIG. 15, the inner diameter of the receptacles of the closure nest corresponds to the inner diameter of the cartridges 5. For closing the upper ends of the cartridges 5, the closures 200 are pushed downward out of the receptacles of the closure nest and into the filling openings at the upper ends of the cartridges 5, while the cartridges are accommodated in the receptacles of the cartridge nest. The closures are pushed down by means of a plurality of adjustable pushing rods 121 of the stoppering machine 120. This stoppering process may be performed row-wise but can also be performed simultaneously for all closures 200 and cartridges 5 held by the nests. For this purpose, both the holding plate 10 of the cartridge nest and the holding plate 60 of stopper nest are sufficiently stiff to ensure the above precise alignment of the closures 200 and cartridges 5 at all stages of the stoppering process.

FIG. 10 shows in a schematic top view an example of a processing apparatus or station for performing a process according to the present invention, as outlined above, under sterile conditions. The processing apparatus 100 has a sterile inner volume 101 with an infeed section at the left-hand side and an outfeed section at the right-hand side thereof. For processing, sterile packaging units as outlined above are fed, via the infeed section, into the sterile inner volume 101. During this infeed step the lids or protective foils of the packaging units are removed so that the tub and nest assemblies accommodating the presterilized cartridges and presterilized closures finally are disposed near the infeed position indicated by reference numeral 102. For processing, the tub and nest assemblies are conveyed by a conveyer 106 along the direction of the arrow shown in FIG. 10 until finally reaching the outfeed position indicated by reference numeral 103. For conveying the nests either the nests are accommodated by holdings frames 40 or similar holding tables or the tubs respectively accommodating a nest are accommodated by holdings frames 40 or similar holding tables. In any case, the upper ends of the cartridges are fed to the processing stations 101 at precisely defined height levels.

The infeed and outfeed sections for the cartridges nests and the closure nests might be at different positions and particularly might be disposed at different height levels.

As an example for a process step, FIG. 10 shows the filling and stoppering of the cartridges accommodated by nests in the holding frames 40. For the filling and stoppering, the nests or tub and nest assemblies for cartridges and for closures are first conveyed to the waiting position 104 and then to the filling and stoppering station 110, where the filling and stoppering process is usually performed row-wise, but may also be performed simultaneously for all cartridges and closures. After filling and stoppering the nests holding the filled and stoppered cartridges or the tub and nest assemblies accommodating the filled and stoppered cartridges are finally conveyed to the outfeed position indicated by reference numeral 103.

During stoppering of the cartridges, when usually large axial forces will be exerted from above onto the cartridges, the symmetric arrangement of the retaining protrusions 15 (see FIG. 2) together with that of the axial ribs 13 ensures a symmetric distribution of such forces with only minor deformation of the general shape of the receptacles 11 and of the retaining protrusions 15 so that both the precise centering and the height levels of the cartridges will be maintained.

Besides filling the sealed cartridges via the filling openings at the upper ends and/or stoppering the sealed cartridges at their upper ends using rubber stoppers, the above procedure may equally be performed for pre gassing or post gassing the cartridges. As can be concluded from FIGS. 2 and 4, the gaps formed between the axial ribs 13 of the receptacles together with the gaps 16 between the retaining protrusions 15 of the receptacles and the access apertures 22 further support a proper gas flow for pre gassing or post gassing of the cartridges when the nest is accommodated in a tub, because a sterilizing gas may flow essentially unhindered from the upper side of the nest towards the bottom side of the nest, if accommodated in a tub.

It will be appreciated that according to the present invention the sealed, particularly pre-crimped, cartridge barrels are entirely of a known form and require no modification as compared to conventional sealed cartridge barrels. Equally the tub is as currently employed in a known prefillable syringe handling system and it is only the nest which has been modified in such a way that it will be interchangeable to a conventional nest of prefillable syringe nest in terms of height level of sealed cartridge barrels in tub as well as on the filling machine table or holding frame. Moreover, as the sealed cartridges allows to use the same height setting of a prefillable syringe filling machine table, the down stand socket of the receptacles ensure that the sealed cartridge barrels are held at the same level of prefillable syringes in a conventional nest.

Thus, the supporting structure for cartridges according to the present invention may be used equally for a manual, semiautomatic or fully-automatic filling and stoppering process, as summarized below:

1) Manual Filling and Stoppering Machine for Prefillable Syringes

Normally this manual filling and stoppering machine as the name suggests is used for filling and stoppering of prefillable syringes in a non-automated process. According to the present invention the customer can fill the medicine into other types of medical devices, i.e. into cartridges having a different axial length, while using the same filling and stoppering machine because the nest and tub assembly according to the present invention enables performing the same processing steps on same machine without any change in filling machine parts and any change in machine setting. Thus, keeping different change parts and different settings and also the requirement of separate validation studies can be avoided, which otherwise will add on to the costs and also will require additional time to change the parts resulting in production loss.

In case of a stoppering machine only the fixture top plate needs to be changed to match the nest design if required without changing the height of the fixture.

2) Semi-Automatic Filling and Stoppering Machine for Prefillable Syringes

Normally this semi-automatic filling and stoppering machine as the name suggests is also used for filling and stoppering of prefillable syringes. According to the present invention the customer can fill the medicine into other types of medical devices, i.e. into cartridges having a different axial length, while using the same filling and stoppering machine because the nest and tub assembly according to the present invention enables performing the same processing steps on same machine without any change in filling machine parts and any change in machine setting, particularly without any change in the filling table height. The same advantages result as outlined above for manual Filling and stoppering machines.

3) Fully-Automatic Filling and Stoppering Machine for Prefillable Syringes

The nested tub for sealed, particularly pre-crimped, pre-sterilized cartridges according to the present invention can be directly fed on existing fully-automatic filling and stoppering machines of prefillable syringes without any setting change in the machine and without adjustment or change in the filling table height and only by replacement of one change part i.e. carrier resting plate to match the nest design if required.

The following further advantages of the inventive nest for cartridges exist:

1) The cartridge nest design is developed in such a way that the top level of the cartridges in the tub and nest is maintained exactly at the same top height as that of prefillable syringe in conventional tub and nest format.
2) Ribs are provided on the top and/or bottom surface of the nest for maintaining the surface of the nest in horizontal position without bending or cave in downwards towards the tub.
3) The retaining protrusions of each socket have a flower type profile (shown in FIGS. 3 and 4) to hold the sealed cartridges at the shoulder portions. The bottom flower type profile is designed in such a way that it can hold the cartridge stably throughout it's processing, especially during stoppering operation where maximum forces are applied on the nest bottom flower type profile. Bottom flower type profile can sustain up to 1,000 N force.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

LIST OF REFERENCE NUMERALS 1 supporting structure for cartridge (also named cartridge nest)
2 supporting structure for cartridge stoppers (also named stopper nest)

3 transport or packaging container for cartridges (also named tub)
3a transport or packaging container for stoppers (also named tub)
4 tub and nest assembly (for cartridges)
4a tub and nest assembly (for stoppers)
5 cartridge
6 sealing lid
10 (planar) holding plate of cartridge nest 1
11 receptacle
12 side wall of receptacle 11 on upper side
13 axial rib
14 side wall of receptacle 11 on bottom side
15 retaining protrusion
16 gap between retaining protrusions 15
17 central opening
20 rounded corner
21 extension
22 gripping aperture
23 side wall of gripping aperture 22
24 guiding web
25 guiding web
26 stiffening web on upper side
27 stiffening web on bottom side
28 stiffening web on bottom side
30 bottom (of tub for cartridges)
30a bottom (of tub for stoppers)
31 lower side wall (of tub for cartridges)
31a lower side wall (of tub for stoppers)
32 supporting step (of tub for cartridges)
32a supporting step (of tub for stoppers)
33 upper side wall (of tub for cartridges)
33a upper side wall (of tub for stoppers)
34 upper flange (of tub for cartridges)
34a upper flange (of tub for stoppers)
35 rounded corner (of tub for cartridges)
35a rounded corner (of tub for stoppers)
36a inner rounded corner (of tub for stoppers)
40 holding frame
41 filling nozzle
42 holding arm for filling array of nozzles 41
43 holding arm for stoppering devices
50 cylindrical body
51 shoulder portion
52 widened upper rim
53 filling opening
54 bottom opening
55 seal
60 supporting plate of stopper nest 2
61 receptacle
62 side wall of receptacle 61
63 upper extension of side wall 62
64 rounded corner
65 upper end of receptacle 61
66 upper fixing protrusion
67 bottom retaining protrusion
70 machine holding frame
71 opening
72 spacer rod
80 bottom holding frame
81 alignment hole
82 spacer rod
83 alignment tip of spacer rod 82
84 opening of central holding frame 80
90 upper holding frame
91 alignment hole
92 receptacle
93 cylindrical side wall
94 bottom protrusion
100 processing apparatus
101 sterile inner volume
102 tub and nest assembly at infeed
103 tub and nest assembly at outfeed
104 nest assembly at waiting position
105 nest assembly at filling station
106 conveyor
110 process station for filling and stoppering
111 downstream processing station
120 stoppering machine
121 pushing rod
200 stopper
201 protrusion
202 recess

The invention claimed is:
1. A transport or packaging container accommodating a plurality of supporting structures for closures, for transporting or packaging closures for closing cartridges for use in pharmaceutical, medical or cosmetic applications, wherein the transport or packaging container is box-shaped and comprises:
a bottom, which is closed or sealed by a seal,
upstanding lower side-walls extending essentially perpendicularly from said bottom,
a circumferential supporting step extending horizontally from said upstanding lower side-walls,
upper side-walls extending upward from said circumferential supporting step, and
a circumferential flange formed at upper ends of the upper side-walls; and
the plurality of supporting structures for closures is accommodated inside the transport or packaging container; wherein
each supporting structure for closures of the plurality of supporting structures for closures comprises:
a planar supporting plate, and
a plurality of tubular receptacles formed by circumferential side walls that are integrally formed with the planar supporting plate, wherein
the plurality of tubular receptacles are disposed in a regular arrangement at the planar supporting plate and protrude from the planar supporting plate; wherein
the closures have a cylindrical shape, consist of a resilient material and are releasably retained in the tubular receptacles of a respective one of the plurality of supporting structures for closures by retaining structures so that the closures are accommodated in the tubular receptacles of the respective one of the plurality of supporting structures for closures completely; wherein
the plurality of supporting structures for closures is accommodated inside the transport or packaging container stacked one above the other, and
an uppermost supporting structure for closures of the plurality of supporting structures for closures does not protrude beyond the circumferential flange formed at the upper ends of the upper side-walls of the transport or packaging container, wherein lower ends of the circumferential side-walls of a respective upper supporting structure for closures of two adjacent supporting structure for closures rest directly on an upper surface of the planar supporting plate of a respective lower supporting structure for closures of the two adjacent supporting structure for closures.

2. The transport or packaging container as claimed in claim 1, wherein an outer diameter of the plurality of tubular receptacles of each supporting structure for closures of the plurality of supporting structures for closures is larger than an inner diameter of the plurality of tubular receptacles of each supporting structure for closures of the plurality of supporting structures for closures so that the circumferential side-walls of the respective upper supporting structure for closures of two adjacent supporting structure for closures do not penetrate into upper ends of the plurality of tubular receptacles of the respective lower supporting structure for closures of the two adjacent supporting structure for closures.

3. The transport or packaging container as claimed in claim 1, wherein the plurality of supporting structures for closures is stacked one above the other without spacers between respective adjacent supporting structures for closures of the plurality of supporting structures for closures, for optimizing the packing density.

4. The transport or packaging container as claimed in claim 1, wherein an edge of a planar supporting plate of a bottommost supporting structure for closures of the plurality of supporting structures for closures is supported on the circumferential supporting step of the transport or packaging container.

5. The transport or packaging container as claimed in claim 4, wherein the transport or packaging container is closed or sealed by a protective foil against the environment, the protective foil being bonded to the circumferential flange formed at the upper ends of the upper side-walls of the transport or packaging container.

6. The transport or packaging container as claimed in claim 5, wherein the protective foil is a gas-permeable plastic film formed by a web of synthetic fibers or a Tyvek® protective film enabling a sterilization of an interior of the transport or packaging container through the protective foil.

7. The transport or packaging container as claimed in claim 4, wherein the plurality of supporting structures for closures is disposed in a space between the circumferential supporting step of the transport or packaging container and the circumferential flange formed at the upper ends of the upper side-walls of the transport or packaging container.

8. The transport or packaging container as claimed in claim 7, wherein the transport or packaging container is closed or sealed by a protective foil against the environment, the protective foil being bonded to the circumferential flange formed at the upper ends of the upper side-walls of the transport or packaging container.

9. The transport or packaging container as claimed in claim 8, wherein the protective foil is a gas-permeable plastic film formed by a web of synthetic fibers or a Tyvek® protective film enabling a sterilization of an interior of the transport or packaging container through the protective foil.

10. The transport or packaging container as claimed in claim 1, wherein the retaining structures are formed on inner sides of the circumferential side walls of the tubular receptacles.

11. The transport or packaging container as claimed in claim 10, wherein the retaining structures comprise protrusions formed on the inner sides of the circumferential side walls of the tubular receptacles.

12. The transport or packaging container as claimed in claim 11, wherein the protrusions are configured to mate to the outer contour of the closures.

13. The transport or packaging container as claimed in claim 12, wherein the protrusions are formed at equal angular distances along the inner sides of the circumferential side walls of the tubular receptacles.

14. The transport or packaging container as claimed in claim 11, wherein the protrusions are formed as circumferential protrusions on the inner sides of the circumferential side walls of the tubular receptacles.

15. The transport or packaging container as claimed in claim 1, wherein
 the plurality of tubular receptacles each comprises upper retaining structures formed at or near an upper end of the tubular receptacles and bottom retaining structures formed at a bottom end of the tubular receptacles, for releasably engaging with the closures for retaining the closures in the tubular receptacles, wherein
 the upper retaining structures are formed as convexly curved protrusions protruding from the inner sides of the circumferential side walls of the tubular receptacles,
 the bottom retaining structures are formed as hook-like protrusions protruding from the inner sides of the circumferential side walls of the tubular receptacles, and
 the bottom retaining structures are beveled on an upper and/or lower side thereof.

16. The transport or packaging container as claimed in claim 15, wherein a distance between the respective upper and bottom retaining structures of each tubular receptacle of the plurality of tubular receptacles is smaller than or equal to the axial length of the closures.

17. A transport or packaging container accommodating a plurality of supporting structures for closures, for transporting or packaging closures for closing cartridges for use in pharmaceutical, medical or cosmetic applications under sterile conditions, wherein
 the transport or packaging container is box-shaped and comprises:
  a bottom, which is closed or sealed by a seal,
  side-walls extending upward essentially perpendicularly to said bottom, and
  a circumferential flange formed at upper ends of the side-walls; and
 the plurality of supporting structures for closures is accommodated inside the transport or packaging container; wherein
 each supporting structure for closures of the plurality of supporting structures for closures comprises a planar supporting plate and a plurality of tubular receptacles formed at a respective planar supporting plate so as to protrude from a surface of the respective planar supporting plate,
 each tubular receptacle of the plurality of tubular receptacles accommodates a closure having a cylindrical shape and consisting of a resilient material, and
 the closures are releasably retained in the tubular receptacles by retaining structures; wherein
 the plurality of supporting structures for closures is accommodated inside the transport or packaging container with the planar supporting plates stacked one above the other, and
 the transport or packaging container is closed or sealed by a protective foil against the environment, which is bonded to the circumferential flange formed at the upper ends of the upper side-walls of the transport or packaging container, wherein
the protective foil is a gas-permeable plastic film formed by a web of synthetic fibers or a Tyvek® protective film enabling a sterilization of an interior of the transport or packaging container through the protective foil, wherein lower ends of the circumferential side-walls of a respective upper supporting structure for closures of two adjacent supporting structure for closures rest directly on an upper surface of the planar supporting plate of a respective lower supporting structure for closures of the two adjacent supporting structure for closures.

18. The transport or packaging container as claimed in claim 17, wherein an edge of a bottommost supporting structure for closures of the plurality of supporting structures for closures is supported on the circumferential supporting step of the transport or packaging container.

\* \* \* \* \*